US010489922B2

(12) United States Patent
Ishikawa et al.

(10) Patent No.: US 10,489,922 B2
(45) Date of Patent: Nov. 26, 2019

(54) INFORMATION PROCESSING APPARATUS, INFORMATION PROCESSING METHOD, AND PROGRAM

(71) Applicant: Sony Corporation, Tokyo (JP)

(72) Inventors: Takanori Ishikawa, Tokyo (JP); Yasuhide Hyodo, Saitama (JP); Kazunari Yoshifuji, Tokyo (JP)

(73) Assignee: Sony Corporation, Tokyo (JP)

( * ) Notice: Subject to any disclaimer, the term of this patent is extended or adjusted under 35 U.S.C. 154(b) by 135 days.

(21) Appl. No.: 15/560,194

(22) PCT Filed: Mar. 16, 2016

(86) PCT No.: PCT/JP2016/058269
§ 371 (c)(1),
(2) Date: Sep. 21, 2017

(87) PCT Pub. No.: WO2016/158404
PCT Pub. Date: Oct. 6, 2016

(65) Prior Publication Data
US 2018/0082432 A1 Mar. 22, 2018

(30) Foreign Application Priority Data
Mar. 30, 2015 (JP) ................................. 2015-068150

(51) Int. Cl.
*G06T 7/32* (2017.01)
*G06T 7/262* (2017.01)
(Continued)

(52) U.S. Cl.
CPC ............ *G06T 7/262* (2017.01); *A61B 5/0077* (2013.01); *A61B 5/02438* (2013.01);
(Continued)

(58) Field of Classification Search
CPC ........... G06T 7/262; G06T 5/003; G06T 7/70; G06T 2207/20201; G06T 2207/30104;
(Continued)

(56) References Cited

U.S. PATENT DOCUMENTS 6,075,905 A * 6/2000 Herman .................... G06K 9/32
348/588
6,888,566 B2 * 5/2005 Larkin .................... H04N 5/145
348/208.4
(Continued)

FOREIGN PATENT DOCUMENTS

JP          10-290791 A    11/1998
JP       2008-538186 A    10/2008
WO   WO 2014/020611 A1    2/2014

OTHER PUBLICATIONS

International Search Report and Written Opinion and English translation thereof dated Jun. 7, 2016 in connection with International Application No. PCT/JP2016/058269.
(Continued)

*Primary Examiner* — Sheela C Chawan
(74) *Attorney, Agent, or Firm* — Wolf, Greenfield & Sacks, P.C.

(57) ABSTRACT

The present technology relates to an information processing apparatus, an information processing method, and a program that can improve the estimation accuracy of a motion amount of an object.
A cross-correlation analysis unit performs a cross-correlation analysis between a first image and a second image obtained by capturing the same object as an object of the first image before the first image, a first motion estimation unit estimates a first motion amount corresponding to a motion blur in the first image, and a second motion estimation unit estimates a second motion amount different from the first motion amount between the first image and the second
(Continued)

image on the basis of a result of the cross-correlation analysis and an estimation result of the first motion amount. The present technology can be applied to, for example, an apparatus for measuring a pulse.

11 Claims, 16 Drawing Sheets

(51) Int. Cl.
*G06T 7/70* (2017.01)
*A61B 5/024* (2006.01)
*A61B 5/00* (2006.01)
*A61B 5/11* (2006.01)
*G06T 5/00* (2006.01)

(52) U.S. Cl.
CPC ........ *A61B 5/02444* (2013.01); *A61B 5/1128* (2013.01); *A61B 5/6801* (2013.01); *A61B 5/7246* (2013.01); *G06T 5/003* (2013.01); *G06T 7/32* (2017.01); *G06T 7/70* (2017.01); *A61B 5/681* (2013.01); *A61B 5/7257* (2013.01); *A61B 2576/00* (2013.01); *G06T 2207/20056* (2013.01); *G06T 2207/20201* (2013.01); *G06T 2207/30104* (2013.01)

(58) Field of Classification Search
CPC ......... G06T 2207/20056; A61B 5/1128; A61B 5/0077; A61B 5/7246; A61B 5/02444; A61B 5/6801; A61B 5/02438; A61B 5/681; A61B 5/7257; A61B 2576/00
USPC ............... 382/232, 243, 236, 278, 107, 151; 348/452, 441, 700, E5.066, E5.077; 375/240.12, 240.16, E7.256, E7.211, 375/E7.105, E7.261, E7.081, 240.17, 375/E7.181, E7.176, E7.15, E7.139, 375/240.02, E7.25
See application file for complete search history.

(56) References Cited

U.S. PATENT DOCUMENTS

| | | | | |
|---|---|---|---|---|
| 6,940,557 | B2 * | 9/2005 | Handjojo | H04N 5/145 348/448 |
| 7,298,868 | B2 * | 11/2007 | Comaniciu | G06T 7/20 382/107 |
| 7,728,909 | B2 * | 6/2010 | Poon | G06T 7/223 348/451 |
| 7,961,954 | B2 * | 6/2011 | Rohaly | G06K 9/6215 340/5.83 |
| 8,345,945 | B2 * | 1/2013 | Song | G06T 7/246 382/131 |
| 9,445,110 | B2 * | 9/2016 | Leontaris | H04N 19/80 |
| 2012/0071769 | A1 | 3/2012 | Dunn et al. | |
| 2013/0144137 | A1 | 6/2013 | Zalevsky et al. | |
| 2015/0049178 | A1 | 2/2015 | Dunn et al. | |

OTHER PUBLICATIONS

International Preliminary Report on Patentability and English translation thereof dated Oct. 12, 2017 in connection with International Application No. PCT/JP2016/058269.

* cited by examiner

INFORMATION PROCESSING APPARATUS, INFORMATION PROCESSING METHOD, AND PROGRAM

CROSS-REFERENCE TO RELATED APPLICATIONS

This application claims the benefit under 35 U.S.C. § 371 as a U.S. National Stage Entry of International Application No. PCT/JP2016/058269, filed in the Japanese Patent Office as a Receiving Office on Mar. 16, 2016, which claims priority to Japanese Patent Application Number JP 2015-068150, filed in the Japanese Patent Office on Mar. 30, 2015, each of which is hereby incorporated by reference in its entirety.

TECHNICAL FIELD

The present technology relates to an information processing apparatus, an information processing method, and a program and, in particular, to an information processing apparatus, an information processing method, and a program that have improved the estimation accuracy of a motion amount of an object.

BACKGROUND ART

In recent years, a pulse measurement apparatus according to an optical technique has become widespread (for example, refer to Patent Document 1). Furthermore, some pulse measurement apparatuses according to an optical technique are of a wearable device type used by being worn on an arm or the like.

CITATION LIST

Patent Document

Patent Document 1: Japanese National Publication of International Patent Application No. 2008-538186

SUMMARY OF THE INVENTION

Problems to be Solved by the Invention

In order to improve wearing feeling of a wearable device type pulse measurement apparatus, it is desirable that the wearable device can be worn somewhat loosely on an arm or the like without being worn too tightly. Meanwhile, when the pulse measurement apparatus is worn loosely, the apparatus moves due to a body motion of a subject and a motion blur occurs in a captured image. Then, the estimation accuracy of a motion amount in an image by a pulse decreases due to the motion blur and, as a result, the measurement accuracy of the pulse decreases.

Therefore, the present technology is intended to improve the estimation accuracy of a motion amount of the object.

Solutions to Problems

An information processing apparatus according to an aspect of the present technology includes a cross-correlation analysis unit that performs a cross-correlation analysis between a first image and a second image obtained by capturing the same object as an object of the first image before the first image, a first motion estimation unit that estimates a first motion amount corresponding to a motion blur in the first image, and a second motion estimation unit that estimates a second motion amount different from the first motion amount between the first image and the second image on the basis of a result of the cross-correlation analysis and an estimation result of the first motion amount.

The second motion estimation unit can be configured to estimate the second motion amount by detecting a motion vector on the basis of a result of the cross-correlation analysis and to limit a region for detecting the motion vector on the basis of an estimation result of the first motion amount.

A spatial frequency analysis unit that analyzes a first spatial frequency distribution of the first image and a second spatial frequency distribution of the second image can be further provided, in which the cross-correlation analysis unit can be configured to perform a cross-correlation analysis between the first image and the second image on the basis of the first spatial frequency distribution and the second spatial frequency distribution.

The first motion estimation unit can be provided with a transfer function calculation unit and an estimation unit, in which the transfer function calculation unit can be configured to calculate a first transfer function representing a characteristic of the motion blur in the first image on the basis of the first spatial frequency distribution and a stationary spatial frequency distribution which is a spatial frequency distribution of an image while the object is substantially stationary, and the estimation unit can be configured to estimate the first motion amount on the basis of the first transfer function.

The transfer function calculation unit can be configured to calculate the transfer function on the basis of a ratio of intensity of each spatial frequency between the first spatial frequency distribution and the stationary spatial frequency distribution.

A state determination unit that sets the stationary spatial frequency distribution to be used next with the first spatial frequency distribution in a case where it is determined that the object is substantially stationary in the first image can be further provided.

A motion blur removing unit that removes a component of a motion blur from the spatial frequency distribution of an image can be further provided, in which the transfer function calculation unit can be configured to calculate a second transfer function representing a characteristic of a motion blur in the second image on the basis of the second spatial frequency distribution and the stationary spatial frequency distribution, the motion blur removing unit can be configure to remove a component of the motion blur in the first image from the first spatial frequency distribution on the basis of the first transfer function and to remove a component of the motion blur in the second image from the second spatial frequency distribution on the basis of the second transfer function, and the cross-correlation analysis unit can be configured to perform a cross-correlation analysis between the first image and the second image on the basis of the first spatial frequency distribution and the second spatial frequency distribution from which the components of the motion blurs have been removed.

The object can be a measurement site for measuring a pulse of a subject, and a pulse measurement unit that measures a pulse of the subject on the basis of an estimation result of the second motion amount can be further provided.

The first motion amount can be a motion amount due to a body motion of the subject, and the second motion amount can be a motion amount due to a pulse of the subject.

An information processing method according to an aspect of the present technology includes a cross-correlation analysis step of performing a cross-correlation analysis between a first image and a second image obtained by capturing the same object as an object of the first image before the first image, a first motion estimation step of estimating a first motion amount corresponding to a motion blur in the first image, and a second motion estimation step of estimating a second motion amount different from the first motion amount between the first image and the second image on the basis of a result of the cross-correlation analysis and an estimation result of the first motion amount.

A program according to an aspect of the present technology causes a computer to execute processes including a cross-correlation analysis step of performing a cross-correlation analysis between a first image and a second image obtained by capturing the same object as an object of the first image before the first image, a first motion estimation step of estimating a first motion amount corresponding to a motion blur in the first image, and a second motion estimation step of estimating a second motion amount different from the first motion amount between the first image and the second image on the basis of a result of the cross-correlation analysis and an estimation result of the first motion amount.

In one aspect of the present technology, a cross-correlation analysis between a first image and a second image obtained by capturing the same object as an object of the first image before the first image is performed, a first motion amount corresponding to a motion blur in the first image is estimated, and a second motion amount different from the first motion amount between the first image and the second image is estimated on the basis of a result of the cross-correlation analysis and an estimation result of the first motion amount.

Effects of the Invention

According to one aspect of the present technology, the estimation accuracy of a motion amount of the object is improved.

Note that, the effects described herein are not necessarily limited and any effects described in the present disclosure may be applied.

MODE FOR CARRYING OUT THE INVENTION

Figure 1:
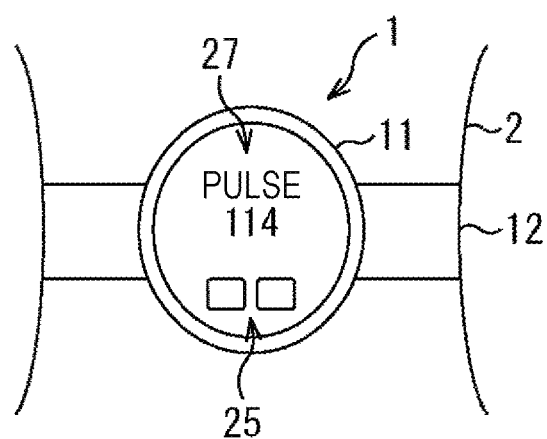
FIG. 1 is an external view illustrating an embodiment of a measurement apparatus to which the present technology is applied.
Figure 2:
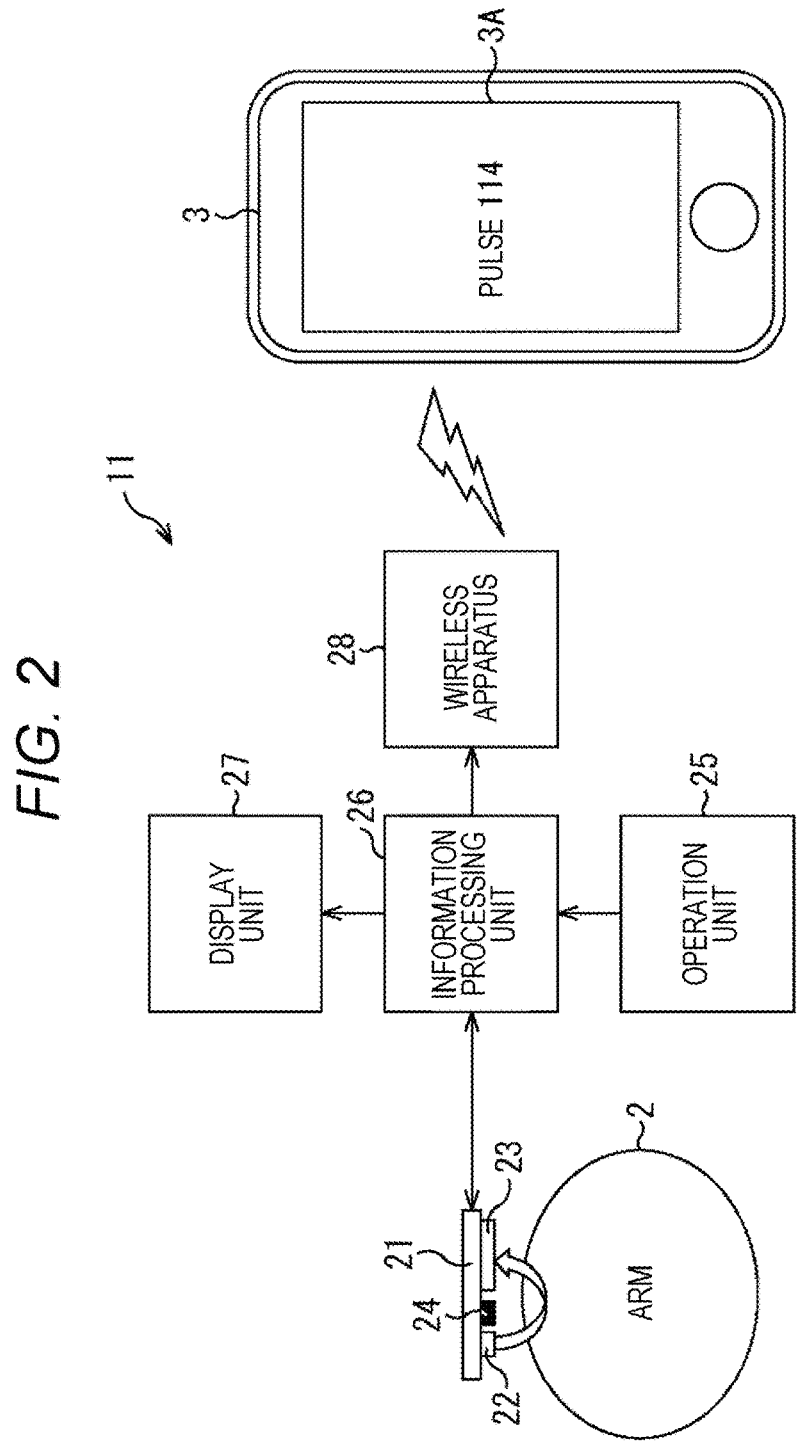
FIG. 2 is a block diagram illustrating a configuration example of a main body unit of the measurement apparatus.

Modes for carrying out the present technology (hereinafter, referred to as embodiments) will be described below. Note that the description will be given in the following order.
1. Embodiments
2. Variations
<1. Embodiments>
{Configuration Example of Measurement Apparatus 1}
FIGS. 1 and 2 illustrate an embodiment of a measurement apparatus to which the present technology is applied. FIG. 1 illustrates a configuration example of the appearance of the measurement apparatus 1. FIG. 2 illustrates a configuration example of a main body unit 11 of the measurement apparatus 1.

The measurement apparatus 1 is a measurement apparatus that measures the pulse of a subject using a speckle technique. The speckle technique is an approach proposed by Professor Zeev Zalevsky of the Bar-Ilan University (BIU) in Israel, in which the motion amount of a speckle pattern in an image is estimated by image analysis to measure variations on a roughened surface.

The measurement apparatus 1 is constituted by the main body unit 11 and a band 12 and is a wristband type measurement apparatus in which the band 12 is worn on an arm (wrist) 2 of the subject like a wristwatch. In addition, the measurement apparatus 1 captures a measurement site by a camera 23 while a light-emitting element 22 irradiates the measurement site which is a part including the pulse on the arm 2 of the subject with illumination light of a predetermined wavelength and, on the basis of the obtained image, measures the pulse of the subject.

The main body unit 11 is configured to include a substrate 21, the light-emitting element 22, the camera 23, a light shielding body 24, an operation unit 25, an information processing unit 26, a display unit 27, and a wireless apparatus 28. The light-emitting element 22, the camera 23, and the light shielding body 24 are provided on the substrate 21.

The light-emitting element 22 is constituted by, for example, a light emitting diode (LED). The light-emitting element 22 irradiates a measurement site which is a site for measuring the pulse on the arm 2 of the subject, with illumination light of a predetermined wavelength.

The camera 23 captures the measurement site of the subject irradiated with the illumination light from the light-emitting element 22 and supplies the obtained image to the information processing unit 26. Note that, since a pulsation movement due to the pulse is minute, an optical system is designed such that a focus position is sufficiently close to the camera 23 but not on an outer surface (roughened surface) of the measurement site. As a result, the camera 23 captures an aerial image of a speckle at the measurement site (hereinafter referred to as a speckle image).

The light shielding body 24 is provided between the light-emitting element 22 and the camera 23 on the substrate 21. The light shielding body 24 prevents the illumination light from the light-emitting element 22 from directly entering the camera 23.

The operation unit 25 is constituted by, for example, various operation members such as buttons and switches and is provided on an outer surface or the like of the main body unit 11. The operation unit 25 is used for operation of the measurement apparatus 1 and supplies a signal indicating operation content to the information processing unit 26.

The information processing unit 26 performs a process of measuring the pulse of the subject on the basis of the speckle image supplied from the camera 23. The information processing unit 26 supplies a measurement result of the pulse to the display unit 27 and the wireless apparatus 28.

The display unit 27 is constituted by, for example, a display apparatus such as a liquid crystal display (LCD) and is provided on the outer surface of the main body unit 11. The display unit 27 displays the measurement result of the pulse of the subject and the like.

The wireless apparatus 28 sends the measurement result of the pulse of the subject to an external apparatus by wireless communication of a predetermined technique. For example, as illustrated in FIG. 2, the wireless apparatus 28 sends the measurement result of the pulse of the subject to a smartphone 3 and displays the measurement result on a screen 3A of the smartphone 3. Note that an arbitrary technique can be adopted as a communication technique of the wireless apparatus 28.

{Configuration Example of Information Processing Unit 26a}

Figure 3:
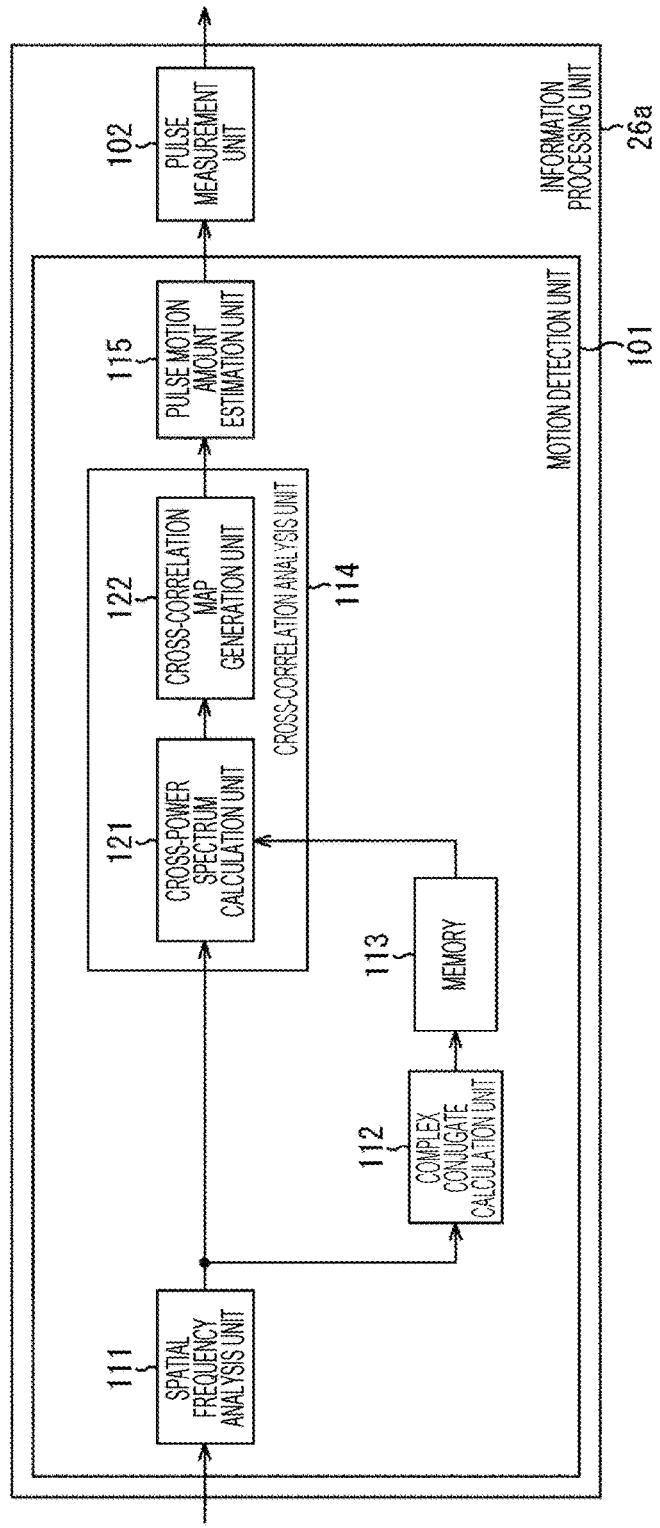
FIG. 3 is a block diagram illustrating a first embodiment of an information processing unit of the measurement apparatus.

FIG. 3 illustrates a configuration example of an information processing unit 26a which is a first embodiment of the information processing unit 26 of the measurement apparatus 1. The information processing unit 26a is configured to include a motion detection unit 101 and a pulse measurement unit 102. The motion detection unit 101 is configured to include a spatial frequency analysis unit 111, a complex conjugate calculation unit 112, a memory 113, a cross-correlation analysis unit 114, and a pulse motion amount estimation unit 115.

The spatial frequency analysis unit 111 analyzes a spatial frequency distribution of the speckle image supplied from the camera 23 and detects a spectral distribution of a spatial frequency of the speckle image. The spatial frequency analysis unit 111 supplies spatial frequency distribution data indicating the spectral distribution of the spatial frequency of the speckle image to the complex conjugate calculation unit 112 and a cross-power spectrum calculation unit 121.

The complex conjugate calculation unit 112 calculates a complex conjugate of the spatial frequency distribution data and stores the obtained complex conjugate data to the memory 113.

The cross-correlation analysis unit 114 performs a cross-correlation analysis between the speckle image of a current frame and the speckle image of an immediately previous frame. The cross-correlation analysis unit 114 is configured to include the cross-power spectrum calculation unit 121 and a cross-correlation map generation unit 122.

On the basis of the spatial frequency distribution data of the current frame and the complex conjugate data of the spatial frequency distribution data of the immediately previous frame, the cross-power spectrum calculation unit 121 calculates a cross-power spectrum between blocks at the same position in the speckle images of the current frame and the immediately previous frame. Note that the size of the block is set to be sufficiently large with respect to the particle size and motion of speckle particles. The cross-power spectrum calculation unit 121 supplies the calculated cross-power spectrum to the cross-correlation map generation unit 122.

The cross-correlation map generation unit 122 performs two-dimensional inverse discrete Fourier transform on the cross-power spectrum and additionally normalizes it to generate a cross-correlation coefficient map. The cross-correlation coefficient map represents a result of the cross-correlation analysis between the speckle image of the current frame and the speckle image of the immediately previous frame. The cross-correlation map generation unit 122 supplies the generated cross-correlation coefficient map to the pulse motion amount estimation unit 115.

On the basis of the cross-correlation coefficient map, the pulse motion amount estimation unit 115 estimates a motion amount due to a pulse (pulsation movement) (hereinafter referred to as a pulse motion amount) between speckle images of adjacent frames. The pulse motion amount estimation unit 115 supplies an estimation result of the pulse motion amount to the pulse measurement unit 102.

The pulse measurement unit 102 measures the pulse of the subject on the basis of the estimation result of the pulse motion amount. The pulse measurement unit 102 supplies the measurement result of the pulse of the subject to the display unit 27 and the wireless apparatus 28.

{First Embodiment of Pulse Measurement Process}

Next, the first embodiment of a pulse measurement process executed by the measurement apparatus 1 will be described with reference to a flowchart in FIG. 4.

In step S1, the camera 23 captures the measurement site. Specifically, as described above with reference to FIG. 2, the camera 23 captures the measurement site of the subject irradiated by the light-emitting element 22 with the illumination light of a predetermined wavelength. Then, the camera 23 supplies a speckle image obtained as a result of the capturing to the spatial frequency analysis unit 111.

In step S2, the spatial frequency analysis unit 111 performs a spatial frequency analysis of the speckle image. For example, the spatial frequency analysis unit 111 performs two-dimensional discrete Fourier transform on the speckle image. Then, the spatial frequency analysis unit 111 supplies the spatial frequency distribution data indicating the spectral distribution of the spatial frequency of the speckle image obtained as a result of the analysis to the complex conjugate calculation unit 112 and the cross-power spectrum calculation unit 121.

In step S3, the cross-power spectrum calculation unit 121 calculates a cross-power spectrum. Specifically, the cross-power spectrum calculation unit 121 reads, from the memory 113, the complex conjugate data of the spatial frequency distribution data of the immediately previous frame. Then, the cross-power spectrum calculation unit 121 performs convolution integral of the spatial frequency distribution data of the current frame and the complex conjugate data of the spatial frequency distribution data of the immediately previous frame to calculate the cross-power spectrum.

Figure 5:
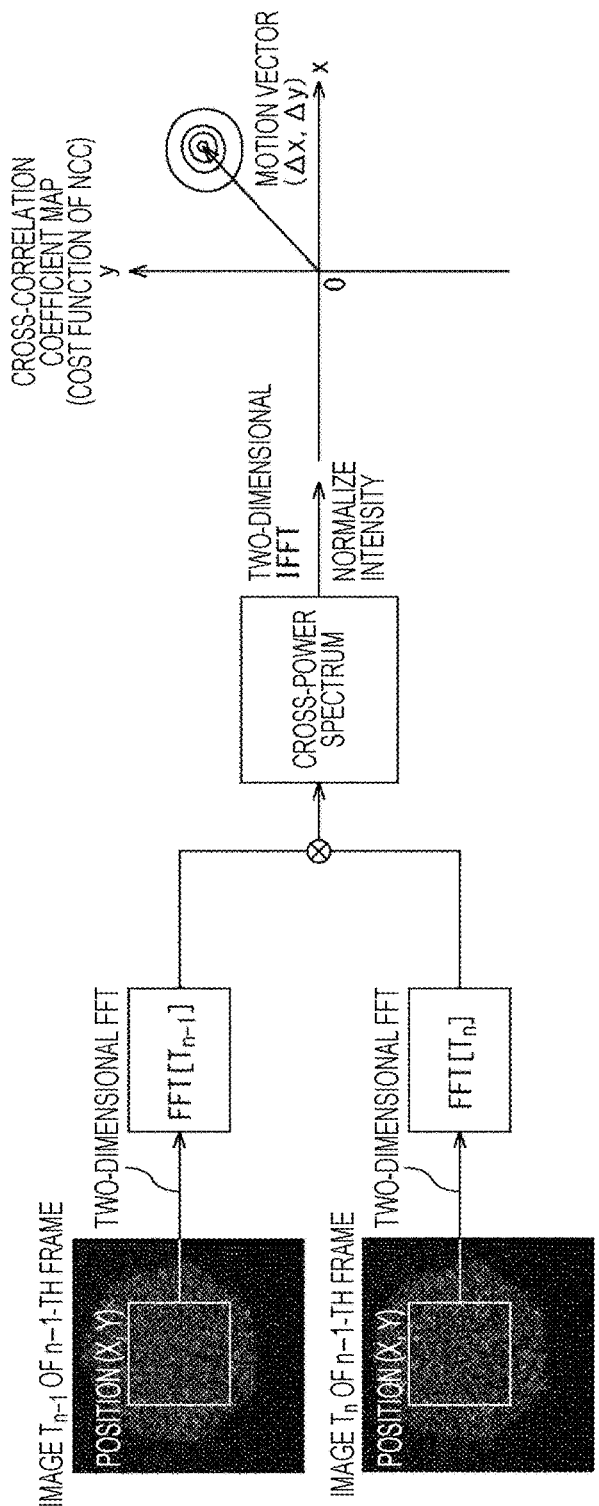
FIG. 5 is a diagram for explaining the first embodiment of the pulse measurement process.

For example, as illustrated in FIG. 5, in a case where the spatial frequency distribution data of a speckle image $T_n$ of a current n-th frame is assumed as $FFT[T_n]$, and the spatial frequency distribution data of a speckle image $T_{n-1}$ of an n−1-th frame is assumed as $FFT[T_{n-1}]$, and the complex conjugate data of the spatial frequency distribution data $FFT[T_{n-1}]$ is assumed as $CFFT[T_{n-1}]$, a cross-power spectrum S is worked out by following formula (1).

$$S=FFT[T_n]*CFFT[T_{n-1}] \quad (1)$$

Note that * in formula (1) indicates the convolution integral.

The cross-power spectrum calculation unit 121 supplies the calculated cross-power spectrum to the cross-correlation map generation unit 122.

In step S4, the cross-correlation map generation unit 122 generates a cross-correlation coefficient map. Specifically, the cross-correlation map generation unit 122 performs the two-dimensional inverse discrete Fourier transform on the cross-power spectrum and additionally normalizes it to generate the cross-correlation coefficient map.

The rightmost diagram in FIG. 5 illustrates an example of the cross-correlation coefficient map. The cross-correlation coefficient map is obtained by mapping a cross-correlation coefficient (correlation value) which is a value of a cost function of normalized cross-correlation (NCC) on a two-dimensional graph having an x-axis and a y-axis. In this example, the cross-correlation coefficients at respective coordinates in the two-dimensional graph are represented by contour lines.

The cross-correlation map generation unit 122 supplies the generated cross-correlation coefficient map to the pulse motion amount estimation unit 115.

In step S5, the pulse motion amount estimation unit 115 estimates the motion amount due to the pulse. Specifically, the pulse motion amount estimation unit 115 detects the coordinates of a position (peak position) where the value of the cross correlation coefficient is highest in the cross-correlation coefficient map. Then, as illustrated in FIG. 5, the pulse motion amount estimation unit 115 detects a vector connecting the origin of the cross-correlation coefficient map and the detected peak position as a motion vector between the speckle image of the immediately previous frame and the speckle image of the current frame.

Herein, the speckle pattern of the speckle image shifts in a planar direction because of the vibration of the outer surface (roughened surface) of the measurement site due to the pulse (pulsation movement). Furthermore, an angular component of the vibration of the outer surface of the measurement site due to the pulse appears as a shift amount of the speckle pattern in the planar direction. Therefore, the pulse motion amount estimation unit 115 estimates components $\Delta x$ and $\Delta y$ of the detected motion vector in an x-axis direction and a y-axis direction as the motion amount of the speckle pattern in the x-axis direction and the y-axis direction due to the pulse (that is, the pulse motion amount).

The pulse motion amount estimation unit 115 supplies the estimation result of the pulse motion amount to the pulse measurement unit 102. The pulse measurement unit 102 stores the estimation result of the pulse motion amount to a memory.

In step S6, the pulse measurement unit 102 determines whether to measure a pulse. For example, in a case where the estimation results of the pulse motion amount are accumulated sufficiently to measure the pulse, the pulse measurement unit 102 determines to measure the pulse and the process proceeds to step S7.

In step S7, the pulse measurement unit 102 measures a pulse. Specifically, in a case where a graph in which pulse motion amounts are arranged in time series is created, substantially the same waveform repeatedly appears at a predetermined cycle in synchronization with the pulse. Therefore, for example, the pulse measurement unit 102 detects this cycle on the basis of the estimation result of the pulse motion amount within an immediately preceding predetermined period and calculates the pulse of the subject on the basis of the detected cycle. The pulse measurement unit 102 supplies the measurement result of the pulse to the display unit 27 and the wireless apparatus 28.

Then, for example, the display unit 27 displays the measurement result of the pulse of the subject. Furthermore, for example, the wireless apparatus 28 sends the measurement result of the pulse of the subject to the smartphone 3 by wireless communication of a predetermined technique and displays the measurement result on the screen 3A of the smartphone 3.

Thereafter, the process proceeds to step S8.

On the other hand, for example, in a case where the estimation results of the pulse motion amount sufficient to measure the pulse are not accumulated yet in step S6, the pulse measurement unit 102 determines not to measure the pulse yet and the process of step S7 is skipped. Then, the process proceeds to step S8.

In step S8, the complex conjugate calculation unit 112 calculates the complex conjugate of the spatial frequency distribution data. That is, the complex conjugate calculation unit 112 calculates the complex conjugate of the spatial frequency distribution data of the speckle image of the current frame and stores the calculated complex conjugate data to the memory 113. This complex conjugate data stored in the memory 113 is used for calculation of the cross-power spectrum in the next frame.

Thereafter, the process returns to step S1 and the processes after step S1 are executed.

As described thus far, the pulse of the subject is measured on the basis of the speckle image. Furthermore, by analyzing the normalized cross-correlation using Fourier transform as a function of similarity, execution of a search process necessary in a case where template matching is used becomes unnecessary. Therefore, the pulse motion amount can be accurately estimated at high speed and, as a result, the pulse of the subject can be accurately measured at high speed.

Figure 6:
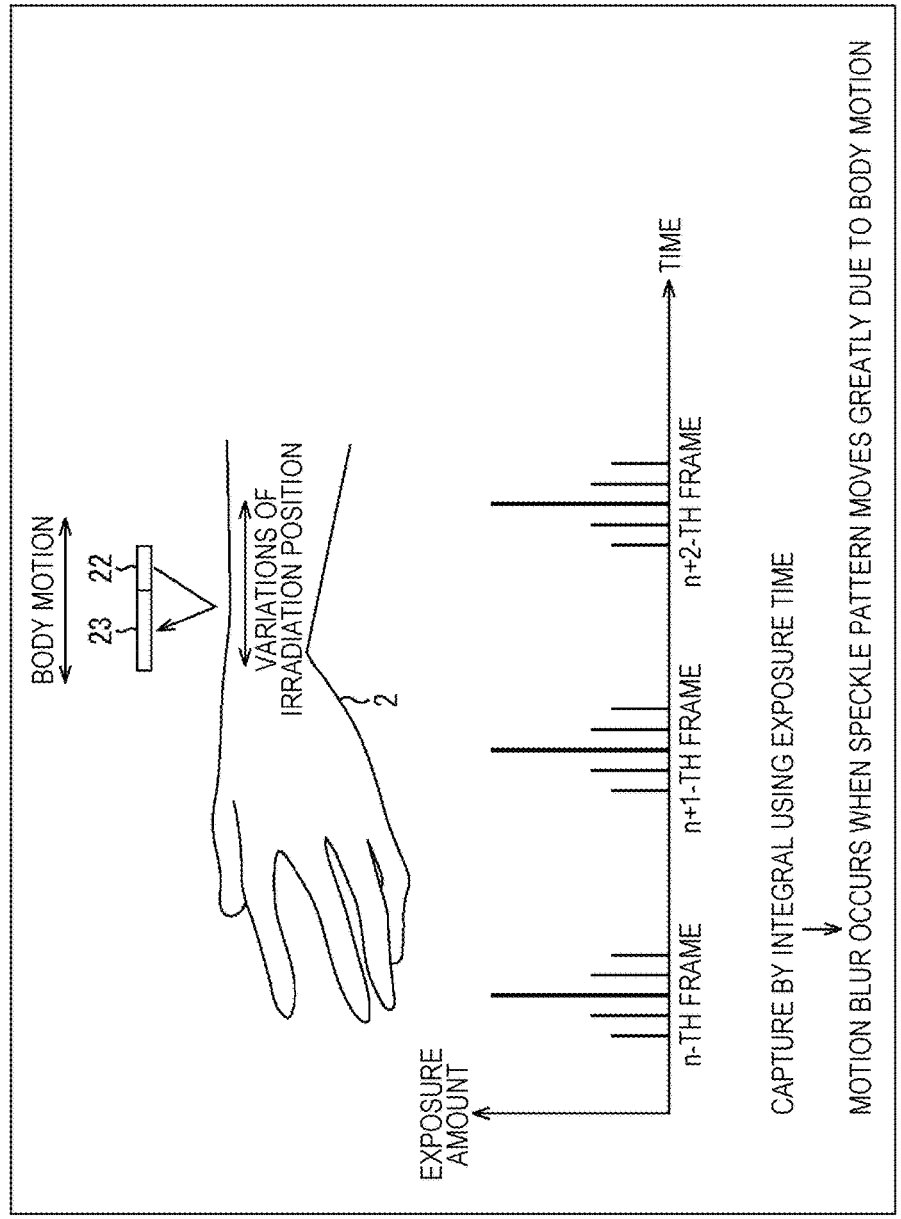
FIG. 6 is a diagram for explaining an occurrence principle of a motion blur due to a body motion.

Herein, as illustrated in the upper diagram of FIG. 6, in a case where the arm 2 of the subject moves, an irradiation position of the illumination light by the light-emitting element 22 varies and, in turn, the measurement site varies. Furthermore, as illustrated in the lower diagram of FIG. 6, since the speckle image is captured by integrating an exposure amount of the camera 23 during an exposure time, a motion blur occurs in the speckle image when the speckle pattern moves greatly due to a body motion.

Figure 7:
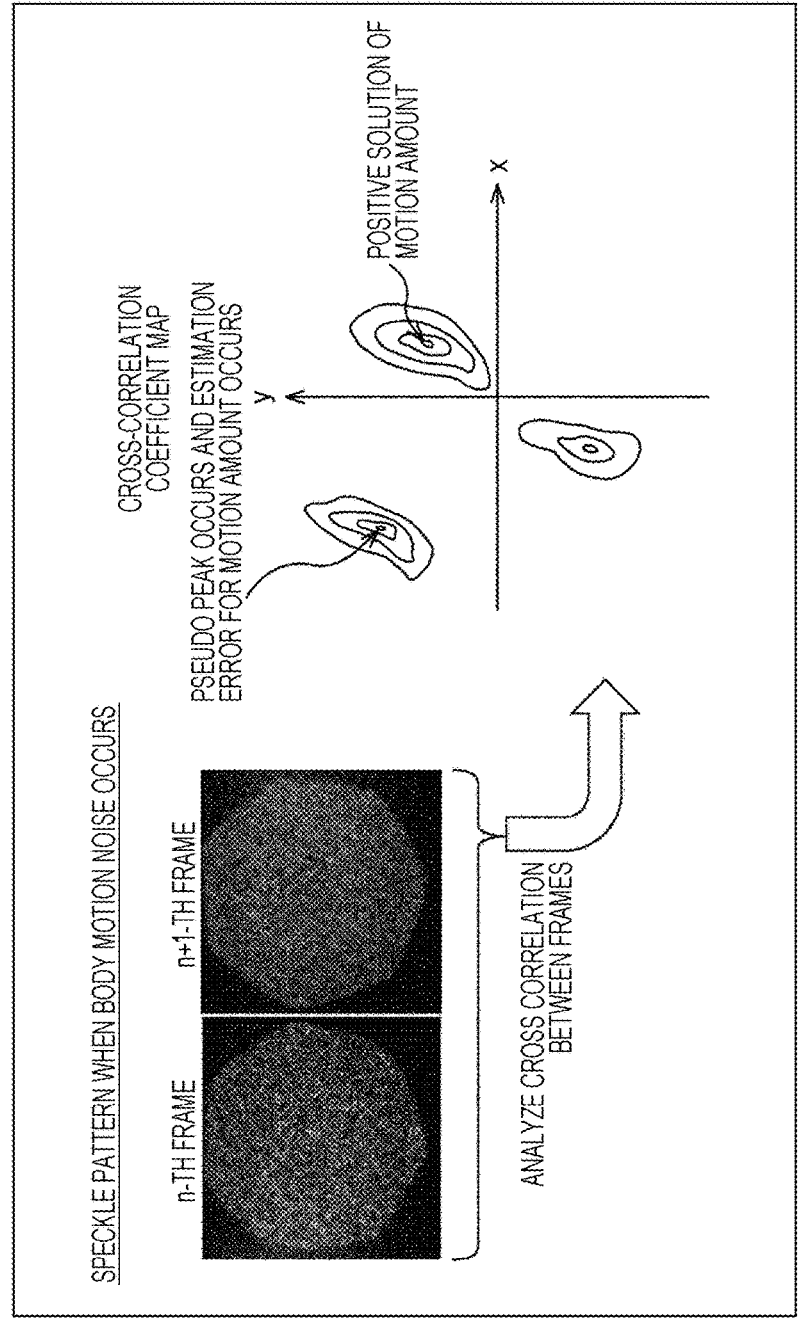
FIG. 7 is a diagram for explaining an occurrence principle of an estimation error for a motion amount.

In addition, in a case where the cross-correlation analysis between adjacent frames is performed at the time of occurrence of a motion blur as described above, the matching accuracy decreases. As a result, as illustrated in FIG. 7, a pseudo peak occurs at a position different from the motion amount caused by the pulse on the cross-correlation coefficient map and an estimation error for the pulse motion amount occurs.

Meanwhile, it is possible to suppress the shift amount of the speckle pattern due to a body motion by devising the optical system but, on the other hand, there is a tradeoff that measurement of small vibrations becomes difficult. For this reason, there is a need for a technology to accurately detect the motion of the speckle pattern with a wide dynamic range from a minute motion to a large motion without being affected by a motion blur.

{Configuration Example of Information Processing Unit 26b}

Figure 8:
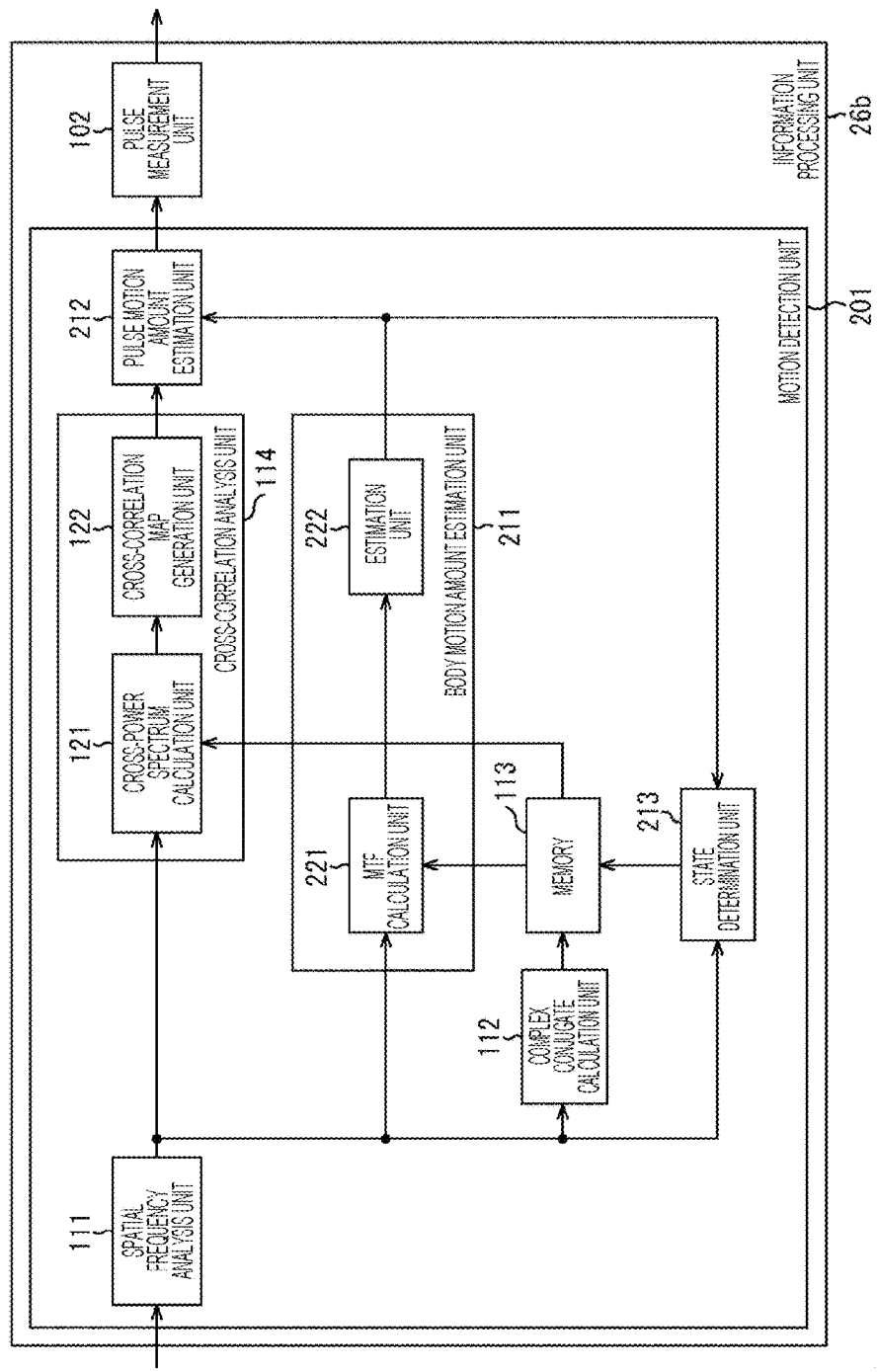
FIG. 8 is a block diagram illustrating a second embodiment of the information processing unit of the measurement apparatus.

FIG. 8 illustrates a configuration example of an information processing unit 26b which is a second embodiment of the information processing unit 26 of the measurement apparatus 1. The information processing unit 26b is intended to reduce the influence of a motion blur in the speckle image, as compared with the information processing unit 26a, while enhancing the estimation accuracy of the pulse motion amount and, as a result, to improve the measurement accuracy of the pulse. Note that, in FIG. 8, parts corresponding to those in FIG. 3 are denoted by the same reference numerals and the description thereof will be omitted as appropriate.

When the information processing unit 26b is compared with the information processing unit 26a in FIG. 3, there is a difference in that a motion detection unit 201 is provided instead of the motion detection unit 101. Compared with the motion detection unit 101, the motion detection unit 201 differs therefrom in that a body motion amount estimation unit 211 and a state determination unit 213 are added and a pulse motion amount estimation unit 212 is added instead of the pulse motion amount estimation unit 115.

The body motion amount estimation unit 211 estimates a motion amount (hereinafter referred to as a body motion amount) and a body motion direction due to a body motion of the subject within the speckle image of each frame. The body motion amount estimation unit 211 is configured to include an MTF calculation unit 221 and an estimation unit 222.

The MTF calculation unit 221 reads, from a memory 113, spatial frequency distribution data in a case where the measurement site is substantially stationary (hereinafter referred to as stationary spatial frequency distribution data). Then, on the basis of the spatial frequency distribution data supplied from a spatial frequency analysis unit 111 and the stationary spatial frequency distribution data, the MTF calculation unit 221 calculates a modulation transfer function (MTF) representing a characteristic of a motion blur in the speckle image. The MTF calculation unit 221 supplies a calculation result of the MTF to the estimation unit 222.

The estimation unit 222 estimates the body motion amount and the body motion direction on the basis of the MTF calculated by the MTF calculation unit 221. The estimation unit 222 supplies the estimation results of the body motion amount and the body motion direction to the pulse motion amount estimation unit 212 and the state determination unit 213.

The pulse motion amount estimation unit 212 estimates the pulse motion amount on the basis of the cross-correlation coefficient map and the estimation results of the body motion amount and the body motion direction. The pulse motion amount estimation unit 115 supplies the estimation result of the pulse motion amount to a pulse measurement unit 102.

On the basis of the estimation result of the body motion amount, the state determination unit 213 determines whether the measurement site is substantially stationary. Furthermore, in a case where it is determined that the measurement site is substantially stationary, the state determination unit 213 updates the stationary spatial frequency distribution data stored in the memory 113 to the spatial frequency distribution data of the current frame.

{Second Embodiment of Pulse Measurement Process}

Next, the second embodiment of the pulse measurement process executed by the measurement apparatus 1 will be described with reference to a flowchart in FIG. 9.

Figure 4:
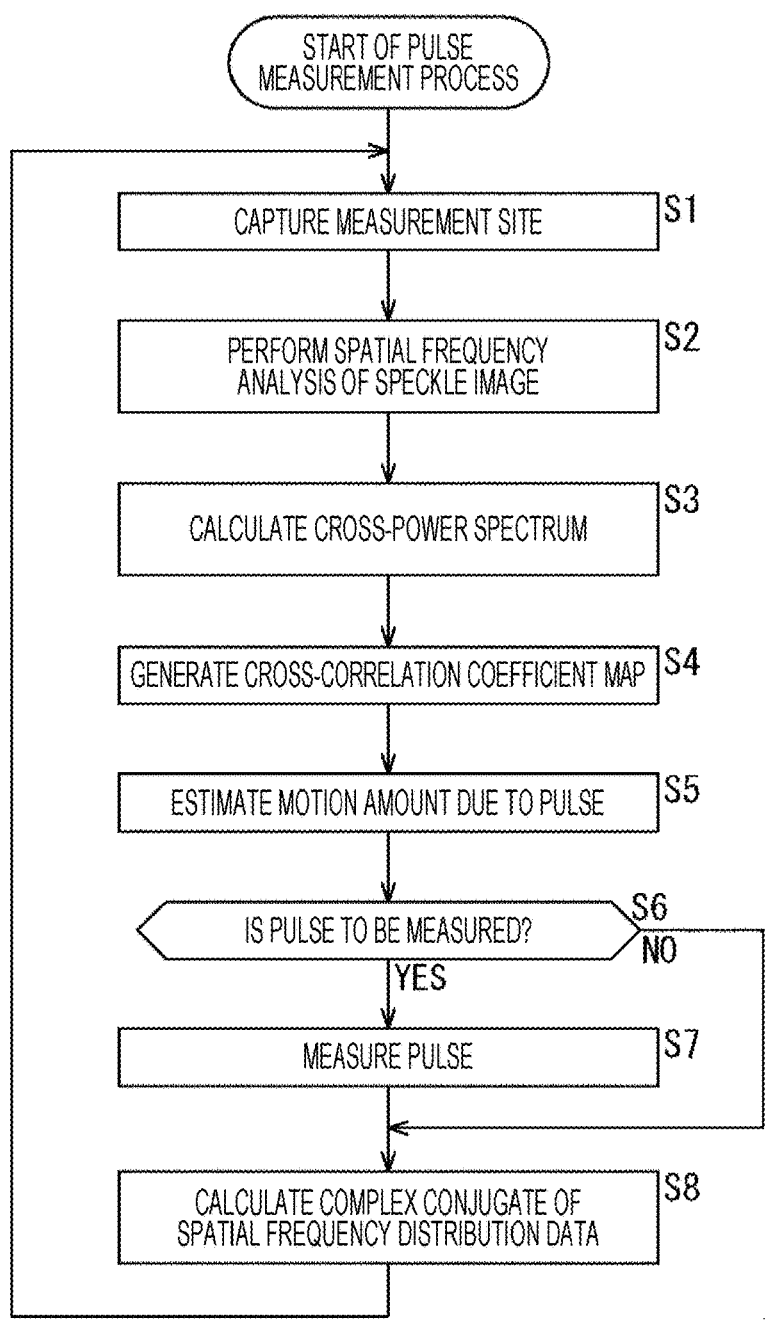
FIG. 4 is a flowchart for explaining the first embodiment of a pulse measurement process.

In step S101, as in the process in step S1 in FIG. 4, the measurement site is captured.

In step S102, the spatial frequency analysis of the speckle image is performed as in the process in step S2 in FIG. 4. The spatial frequency analysis unit 111 supplies the spatial frequency distribution data obtained as a result of the analysis to a complex conjugate calculation unit 112, a cross-power spectrum calculation unit 121, the state determination unit 213, and the MTF calculation unit 221.

In step S103, the cross-power spectrum is calculated as in the process in step S3 in FIG. 4.

In step S104, the cross-correlation coefficient map is generated as in the process in step S4 in FIG. 4.

In step S105, the MTF calculation unit 221 calculates the MTF.

In step S106, the estimation unit 222 estimates the motion amount due to a body motion.

In step S107, the pulse motion amount estimation unit 212 estimates the motion amount due to the pulse.

Herein, details of the processes in steps S105 to S107 will be described with reference to FIGS. 10 to 13.

As described above, in a case where the pulse motion amount is estimated using the cross correlation between adjacent frames, a motion blur occurring due to a body motion of the subject becomes a factor of an error.

Meanwhile, an approach of estimating the motion amount of an object using the motion blur is widely known. Herein, an occurrence principle of a motion blur will be described with reference to FIG. 10.

A point spread function (PSF) indicating the amount of motion blur in the speckle image is deduced by performing the convolution integral on a PSF $h_{opt(Clens)}(x,y)$ by a lens characteristic Clens of the camera 23 and a PSF $h_{opt(V,Texp)}(x,y)$ by a motion amount v and an exposure time Texp of the camera 23. The motion amount v corresponds to a motion amount of the speckle pattern occurring due to a body motion of the subject (body motion amount) within the exposure time.

When a PSF indicating this amount of motion blur is assumed as $h_{(v,Clens,Texp)}(x, y)$, a speckle image z2 in which a motion blur has occurred is obtained by performing the convolution integral on the speckle image z1 during a stationary state with the PSF $h_{(v,Clens,Texp)}(x, y)$. When this is expressed by mathematical formulas, following formulas (2) and (3) are obtained.

[Mathematical Formula 1]

$$z2(x,y) = \iint_D h_{(v,Clens,Texp)}(x-x_o, y \times y_o) z1(x,y) dx_o dy_o \quad (2)$$

$$h_{(v,Clens,Texp)}(x,y) = h_{opt(Clens)}(x,y) * h_{mot(v,Texp)}(x,y) \quad (3)$$

By applying this principle, the PSF $h_{(v,Clens,Texp)}(x, y)$ is estimated from the speckle image in which a motion blur has occurred and then, the characteristics of camera 23 (the lens characteristic and the exposure time) are applied to the estimated PSF $h_{(v,Clens,Texp)}(x, y)$, whereby the motion amount v can be found out.

Meanwhile, the aerial image of the speckle shifts horizontally within a space while maintaining a texture (spatial frequency distribution). By focusing on this, the body motion amount estimation unit 211 estimates the body motion amount by finding out the MTF representing the characteristic of the motion blur, rather than directly finding out the PSF. Note that the aerial image of the speckle mentioned herein is an optical image on a space in the real world and it is necessary to pay attention to the fact that the aerial image is different from the speckle image captured by the camera 23.

Figure 11:
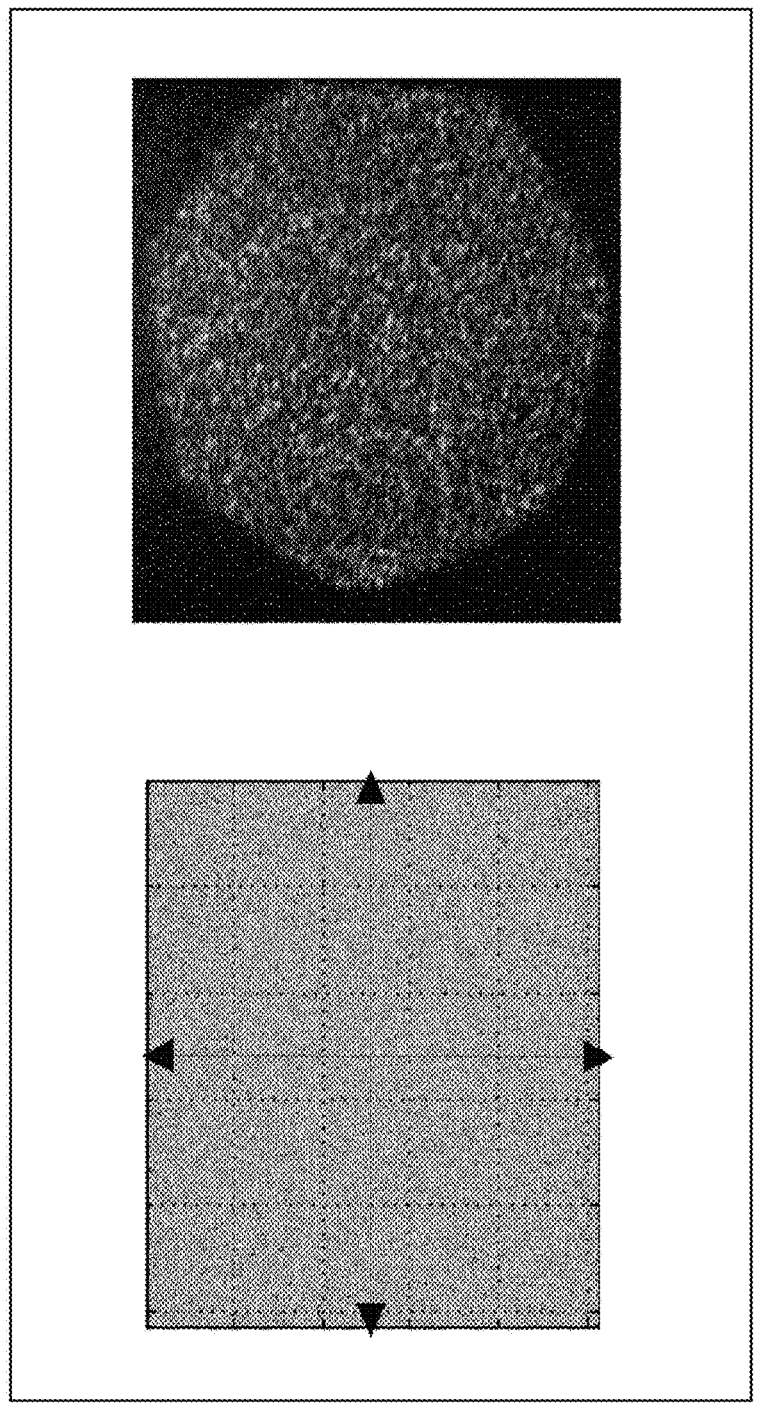
FIG. 11 is a diagram illustrating an example of a speckle image and a spatial frequency distribution during a stationary state.
Figure 12:
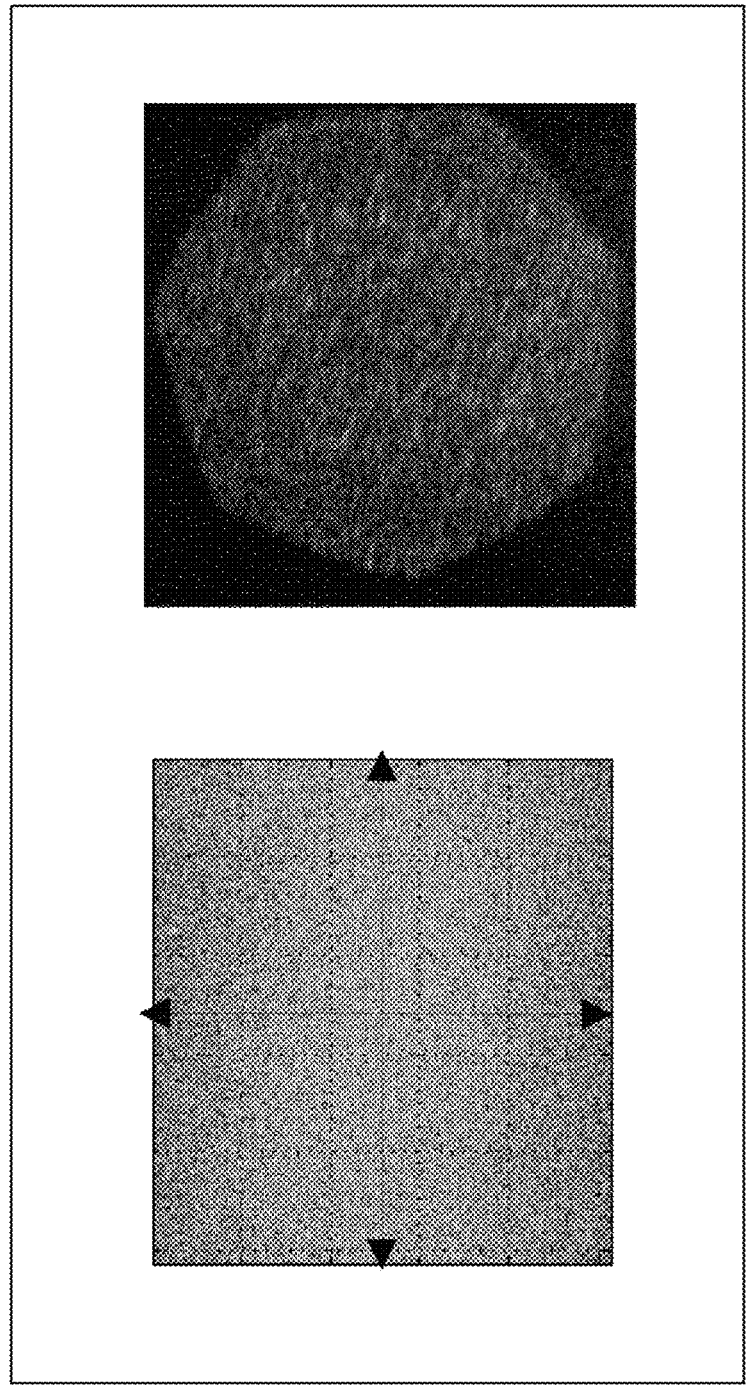
FIG. 12 is a diagram illustrating an example of a speckle image and a spatial frequency distribution during a body motion.

FIG. 11 illustrates an example of a speckle image during a stationary state (upper side) and its spatial frequency distribution (lower side). FIG. 12 illustrates an example of a speckle image during a body motion (upper side) and its spatial frequency distribution (lower side).

The speckle image during a stationary state has a texture such as white noise and, when Fourier transform is performed thereon, the spectrum is distributed substantially uniformly over the entire band of the spatial frequency. This can also be explained in principle from a mathematical formula obtained by Fourier transforming a Gaussian distribution.

On the other hand, in the spatial frequency distribution of the speckle image during a body motion, a high-frequency component decreases and a low-frequency component increases in the body motion direction. Meanwhile, the spatial frequency distribution in a direction perpendicular to the body motion direction hardly changes from the stationary state. Furthermore, it is known that the degradation of the MTF shifts toward a lower frequency side of the spatial frequency as the body motion (the motion amount v) increases. Therefore, a low frequency value of the spatial frequency of the MTF decreases only in the body motion direction.

Therefore, the body motion amount estimation unit 211 estimates the body motion amount (an unsigned vector) by detecting a spatial frequency at which the value of the MTF is equal to or less than a predetermined threshold value. Specifically, when above-described formula (2) is transformed into a function in a spatial frequency domain by Fourier transform, following formula (4) is obtained.

[Mathematical Formula 2]

$$Z2(\omega_x,\omega_y)=H_{(v,Clens,Texp)}(\omega_x,\omega_y)Z1(\omega_x,\omega_y) \quad (4)$$

Note that Z1 is a result of the Fourier transform of the speckle image z1 during a stationary state, Z2 is a result of the Fourier transform of the speckle image z2 during a body motion, $\omega_x$ is an angular frequency in the x-axis direction, and $\omega_y$ is an angular frequency in the y-axis direction. Furthermore, $H_{(v,Clens,Texp)}(\omega_x,\omega_y)$ is a result of the Fourier transform of the PSF $h_{(v,Clens,Texp)}(x,y)$ representing the motion blur and indicates a contrast response of the MTF representing the characteristic of the motion blur of each spatial frequency. Herein, by focusing on a spectral characteristic of formula (4), formula (4) can be modified into following formula (5).

[Mathematical Formula 3]

$$|H_{(v,Clens,Texp)}(\omega_x,\omega_y)|=|Z2(\omega_x,\omega_y)|/|Z1(\omega_x,\omega_y)| \quad (5)$$

That is, $|H_{(v,Clens,Texp)}(\omega_x,\omega_y)|$ indicating a spatial frequency characteristic of the MTF representing the characteristic of the motion blur is expressed by a ratio of the intensity of each spatial frequency between the spatial frequency distribution during a body motion and the stationary spatial frequency distribution. It is possible to estimate an approximate body motion amount by detecting a spatial frequency at which the value of this $|H_{(v,Clens,Texp)}(\omega_x,\omega_y)|$ is equal to or less than a predetermined threshold value.

Additionally, by using $|H_{mot(v,Texp)}(\omega_x,\omega_y)|$ in following formula (6) obtained by modifying formula (5), the body motion amount can be estimated in more detail.

[Mathematical Formula 4]

$$|H_{mot(v,Texp)}(\omega_x,\omega_y)|=|Z_2(\omega_x,\omega_y)|/|Z_1(\omega_x,\omega_y)|1 \\ /|H_{opt(Clens)}(\omega_x,\omega_y)| \quad (6).$$

Note that $|H_{mot(v,Texp)}(\omega_x,\omega_y)|$ is a result of the Fourier transform of the PSF $h_{mot(v,Texp)}$ by the motion amount v and the exposure time Texp of the camera 23 and $|H_{opt(Clens)}(\omega_x,\omega_y)|$ is a result of the Fourier transform of the PSF $h_{opt(Clens)}(x,y)$ by the lens characteristic Clens of the camera 23. Therefore, $|H_{mot(v,Texp)}(\omega_x,\omega_y)|$ is obtained by removing the influence of a blur caused by the lens from $|H_{(v,Clens,Texp)}(\omega_x,\omega_y)|$.

In step S105, the MTF calculation unit 221 reads, from the memory 113, the spatial frequency distribution data of the speckle image during a stationary state (stationary spatial frequency distribution data). This stationary spatial frequency distribution data corresponds to Z1 ($\omega_x$, $\omega_y$) in formulas (5) and (6).

Then, the MTF calculation unit 221 calculates, for example, $|H_{(v,Clens,Texp)}(\omega_x,\omega_y)|$ on the basis of formula (5) or $|H_{mot(v,Texp)}(\omega_x, \omega_y)|$ on the basis of formula (6), as the spatial frequency characteristic of the MTF representing the characteristic of the motion blur. Note that the spatial frequency distribution data of a spectral image of the current frame is used for Z2 ($\omega_x$, $\omega_y$) in formulas (5) and (6).

The MTF calculation unit 221 supplies a calculation result of $|H_{(v,Clens,Texp)}(\omega_x,\omega_y)|$ or $|H_{mot(v,Texp)}(\omega_x,\omega_y)|$ to the estimation unit 222.

Note that, hereinafter, $|H\ h_{(v,Clens,Texp)}(\omega_x,\omega_y)|$ or $|H_{mot(v,Texp)}(\omega_x,\omega_y)|$ calculated by the MTF calculation unit 221 is collectively referred to as an MTF spatial frequency characteristic.

In step S106, the estimation unit 222 detects a spatial frequency at which the value of the MTF spatial frequency characteristic calculated by the MTF calculation unit 221 is equal to or less than a predetermined threshold value. Then, the estimation unit 222 estimates the body motion amount and the direction of the body motion on the basis of the detection result.

Specifically, data indicating how much the value of each spatial frequency of the MTF spatial frequency characteristic ($|H_{(v,Clens,Texp)}$ ($\omega_x$, $\omega_y$)| or $|H_{mot(v,Texp)}(\omega_x, \omega_y)$ degrades (decreases) with respect to the motion amount of the object is evaluated beforehand on the basis of parameters of the camera 23. Then, the estimation unit 222 holds this data and estimates the body motion amount on the basis of the spatial frequency at which the value of the MTF spatial frequency characteristic is equal to or less than the predetermined threshold value. Furthermore, the estimation unit 222 estimates the body motion direction by working out a region where the value of the MTF spatial frequency characteristic is equal to or less than the predetermined threshold value.

The estimation unit 222 supplies the estimation results of the body motion amount and the body motion direction to the pulse motion amount estimation unit 212 and the state determination unit 213.

In step S107, for example, the pulse motion amount estimation unit 115 detects a peak position at which the value of the cross-correlation coefficient is equal to or more than a predetermined threshold value in the cross-correlation coefficient map. Next, the pulse motion amount estimation unit 115 detects a motion vector connecting the origin of the cross-correlation coefficient map and the detected peak position. Next, the pulse motion amount estimation unit 115 excludes a motion vector close to the body motion amount and the body motion direction estimated by the estimation unit 222 from among the detected motion vectors. Then, the pulse motion amount estimation unit 115 selects one of the remaining motion vectors and estimates components of the selected motion vector in the x-axis direction and the y-axis direction as the pulse motion amount in the x-axis direction and the y-axis direction.

Figure 13:
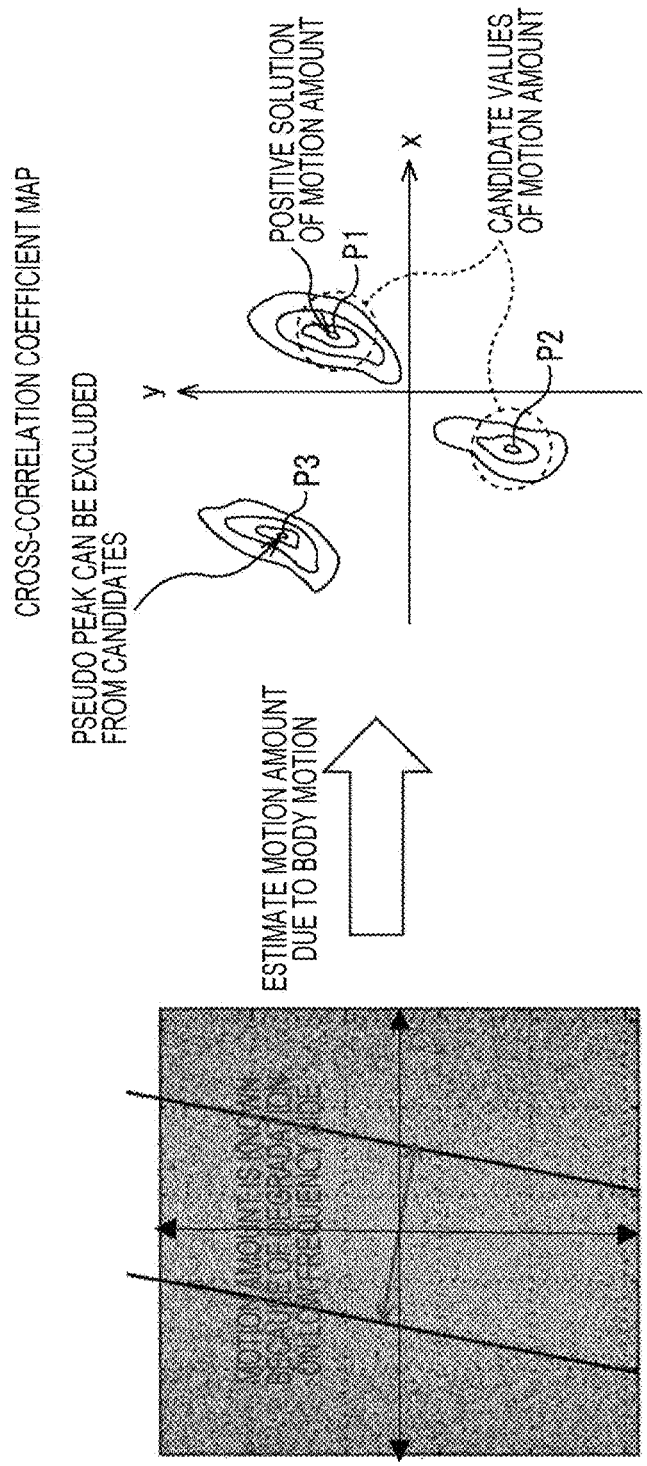
FIG. 13 is a diagram for explaining a method for estimating a motion amount.

For example, in the example of the cross-correlation coefficient map on the right side of FIG. 13, three peaks P1 to P3 appear. Meanwhile, as illustrated in the diagram on the left side of FIG. 13, the body motion direction is a direction diagonally upward slightly to the left and thus, among motion vectors connecting the origin of the cross-correlation coefficient map and the peaks P1 to P3, the motion vector connecting the origin and the peak P3 is excluded from the candidates. That is, the peak P3 is excluded as a pseudo peak. Then, the pulse motion amount estimation unit 115 selects one of the motion vector connecting the origin and the peak P1 and the motion vector connecting the origin and the peak P2. For example, the pulse motion amount estimation unit 115 selects a peak having a larger value from among the peak P1 and the peak P2 and estimates the pulse motion amount on the basis of a motion vector connecting the origin and the selected peak.

Note that, in a case where, for example, the estimation accuracy of the body motion amount is not secured, a region for detecting a peak candidate used for the estimation of the pulse motion amount (hereinafter referred to as a peak detection region) may be limited, for example. For example, a region of which the width in the body motion direction is twice the body motion amount with the origin of the cross-correlation coefficient map as the center (e.g., a region having a similar shape to that of a region between two diagonal lines in the diagram on the left side of FIG. 13) may be set as the peak detection region.

In this manner, by limiting the peak detection region, it is possible to reliably exclude the pseudo peak from the peak detection region and it is possible to enhance the robustness against the body motion in the estimation of the pulse motion amount.

Alternatively, for example, the pulse motion amount estimation unit 115 generates a motion candidate weight map according to the degree of degradation of the MTF spatial frequency characteristic. For example, the weight is set to a value in the range of 0.0 to 1.0.

The pulse motion amount estimation unit 115 corrects the cross-correlation coefficient map by multiplying the cross-correlation coefficient of each coordinate in the cross-correlation coefficient map by the weight of each coordinate in the motion candidate weight map. Then, for example, the pulse motion amount estimation unit 115 estimates the pulse motion amount on the basis of the motion vector connecting the origin and the peak position at which the value of the cross-correlation coefficient is highest in the corrected cross-correlation coefficient map.

The pulse motion amount estimation unit 115 supplies an estimation result of the pulse motion amount to the pulse measurement unit 102. The pulse measurement unit 102 stores data indicating the estimation result of the pulse motion amount to a memory (not illustrated).

Then, in steps S108 to S110, similar processes to those in steps S6 to S8 in FIG. 4 are executed.

In step S111, the state determination unit 213 determines whether the measurement site is stationary. For example, in a case where the body motion amount estimated by the estimation unit 222 is less than a predetermined threshold value, the state determination unit 213 determines that the measurement site is stationary and the process proceeds to step S112.

Note that this threshold value is set to a sufficiently small value, for example, to the extent that a motion blur occurring due to a body motion amount less than this threshold value does not affect the estimation result of the pulse motion amount.

In step S112, the state determination unit 213 updates the spatial frequency distribution data during a stationary state. That is, the state determination unit 213 stores the spatial frequency distribution data of the speckle image of the current frame to the memory 113. Furthermore, the state determination unit 213 deletes the current stationary spatial frequency distribution data from the memory 113. As a result, the spatial frequency distribution data of the speckle image of the current frame is set to the stationary spatial frequency distribution data to be used next.

Since it is assumed that the state of the external light and the measurement site will vary during the measurement of the pulse, the estimation accuracy of the body motion amount is improved by updating the stationary spatial frequency distribution data every time the stationary state is detected as described above.

Note that, since the stationary spatial frequency distribution data is used only for working out the MTF spatial frequency characteristic, the state determination unit 213 can store only the value of a spectral component of each spatial frequency to the memory 113. Therefore, it is sufficient to store only real number data and thus, the necessary storage capacity is only about half that in the case of storing complex number data as well.

Thereafter, the process returns to step S101 and the processes after step S101 are executed.

On the other hand, in a case where the body motion amount estimated by the estimation unit 222 is equal to or more than the predetermined threshold value in step S111, the state determination unit 213 determines that the measurement site is not stationary and the process returns to step S101. Thereafter, the processes after step S101 are executed.

As described thus far, the influence of the motion blur can be reduced, the estimation accuracy of the pulse motion amount can be enhanced, and the measurement accuracy of the pulse can be improved.

Furthermore, the larger the body motion is, the easier it is to detect the body motion amount. It is thus possible to compensate for the weakness of motion estimation by the cross-correlation analysis.

Additionally, it is possible to feed back parameters of the lens and the exposure time of the camera 23 to specifications of an image sensor of the camera 23. Therefore, the estimation accuracy of the pulse motion amount can be advanced in line with an application from the viewpoints of both the image sensor and a signal process.

{Configuration Example of Information Processing Unit 26c}

Figure 14:
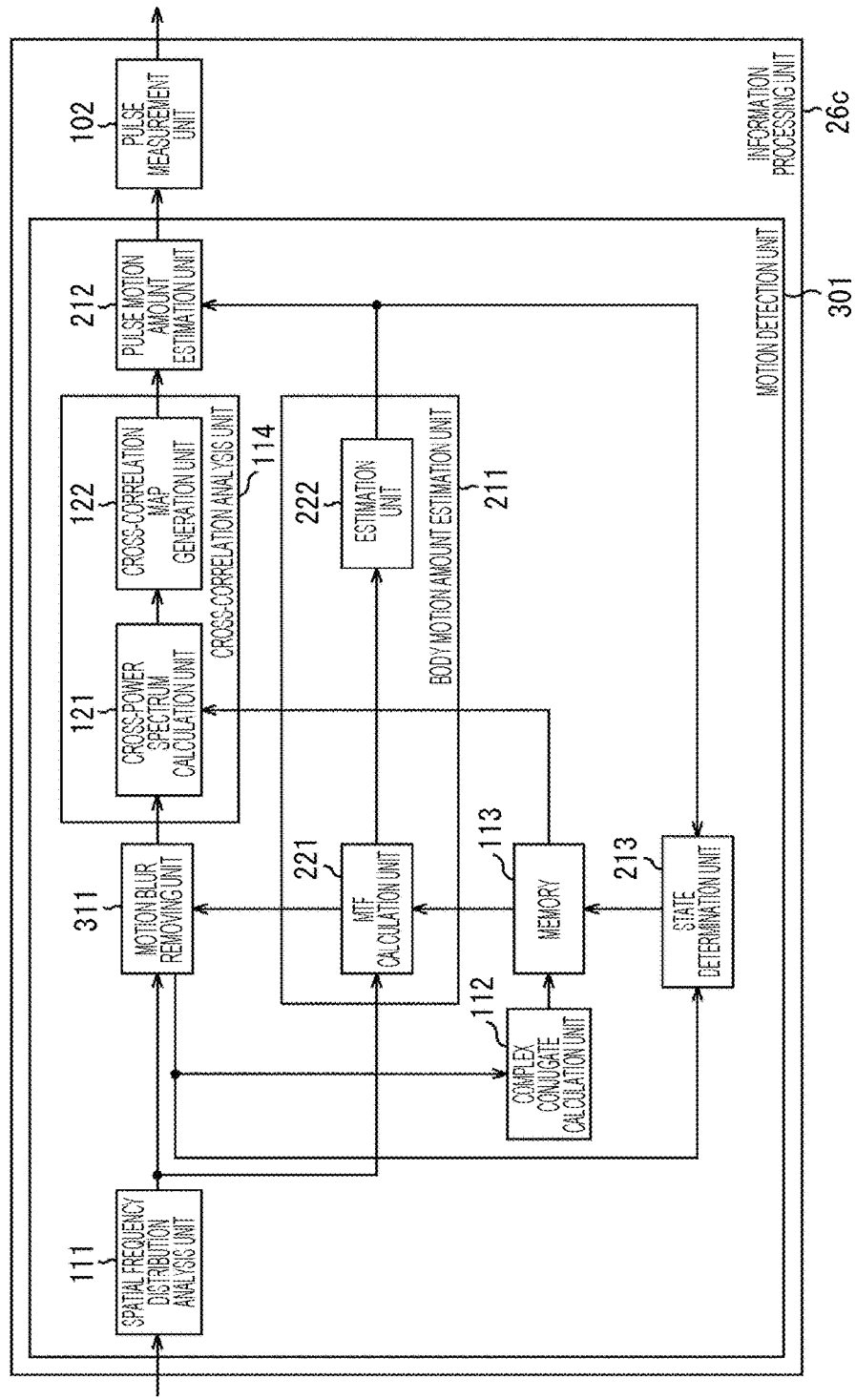
FIG. 14 is a block diagram illustrating a third embodiment of the information processing unit of the measurement apparatus.

FIG. 14 illustrates a configuration example of an information processing unit 26c which is a third embodiment of the information processing unit 26 of the measurement apparatus 1. Note that, in FIG. 14, parts corresponding to those in FIG. 8 are denoted by the same reference numerals and the description thereof will be omitted as appropriate.

When the information processing unit 26c is compared with the information processing unit 26b in FIG. 8, there is a difference in that a motion detection unit 301 is provided instead of the motion detection unit 201. Compared with the motion detection unit 201, the motion detection unit 301 differs therefrom in that a motion blur removing unit 311 is added.

The motion blur removing unit 311 removes a motion blur component from the spatial frequency distribution data on the basis of the MTF spatial frequency characteristic supplied from an MTF calculation unit 221. The motion blur removing unit 311 supplies the spatial frequency distribution data from which the motion blur component has been removed to a complex conjugate calculation unit 112, a cross-power spectrum calculation unit 121, and a state determination unit 213.

{Second Embodiment of Pulse Measurement Process}

Figure 15:
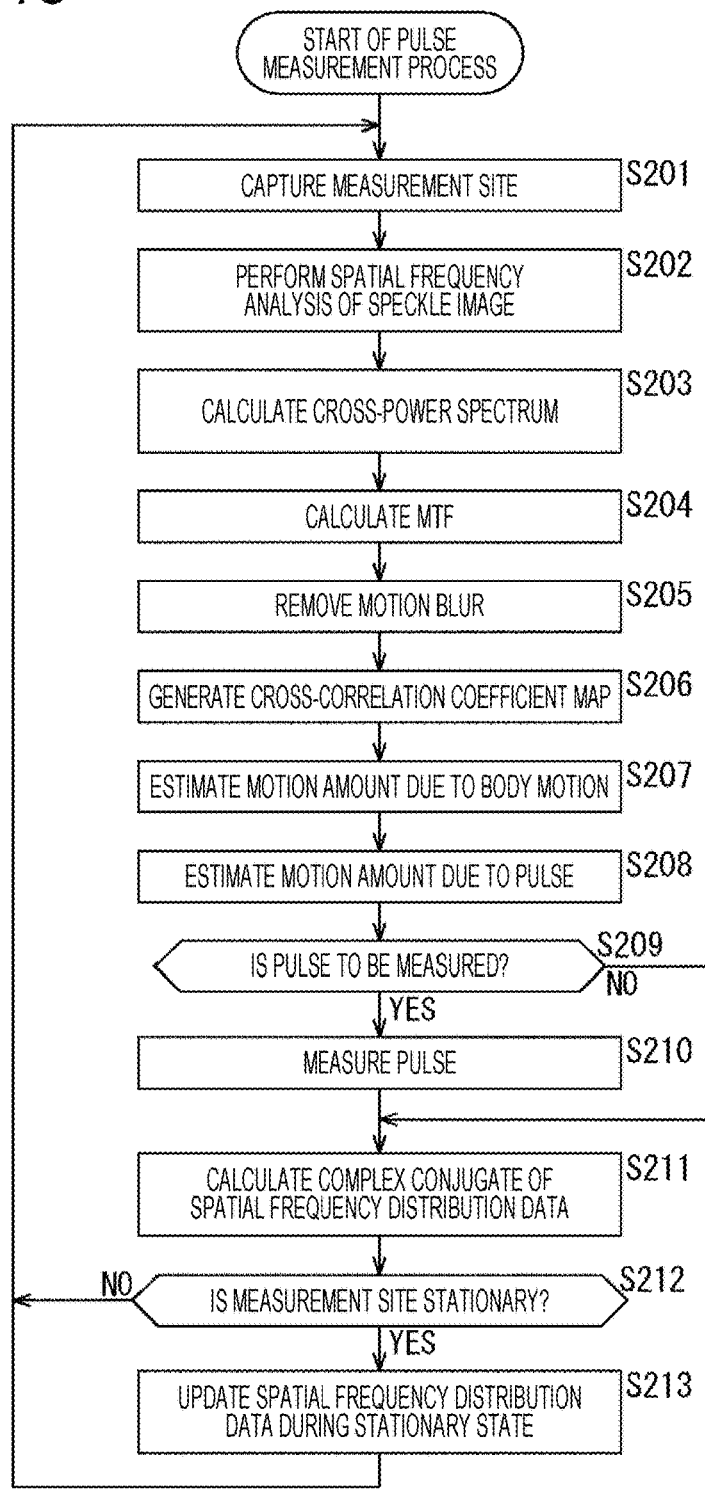
FIG. 15 is a flowchart for explaining the third embodiment of the pulse measurement process.

Next, the third embodiment of the pulse measurement process executed by the measurement apparatus 1 will be described with reference to a flowchart in FIG. 15.

Figure 9:
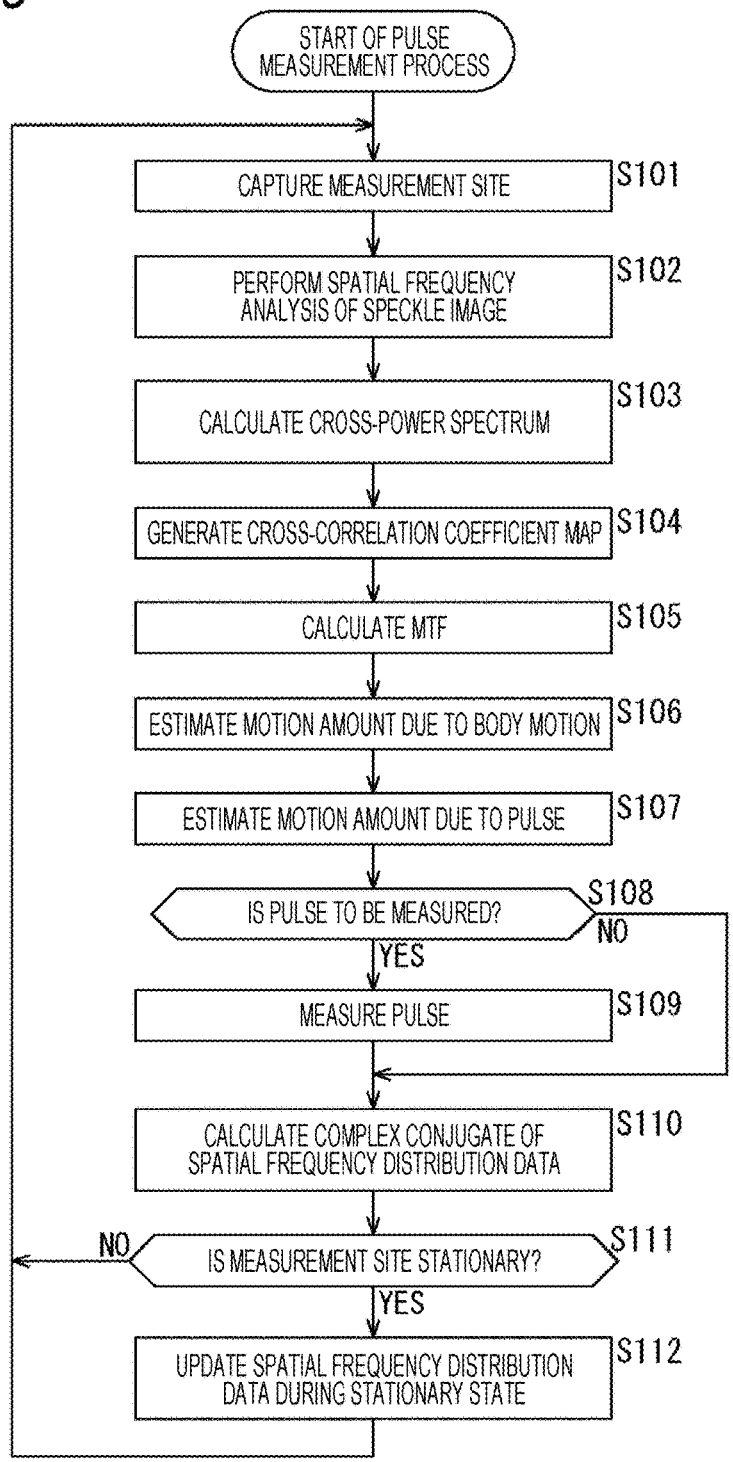
FIG. 9 is a flowchart for explaining the second embodiment of the pulse measurement process.
Figure 10:
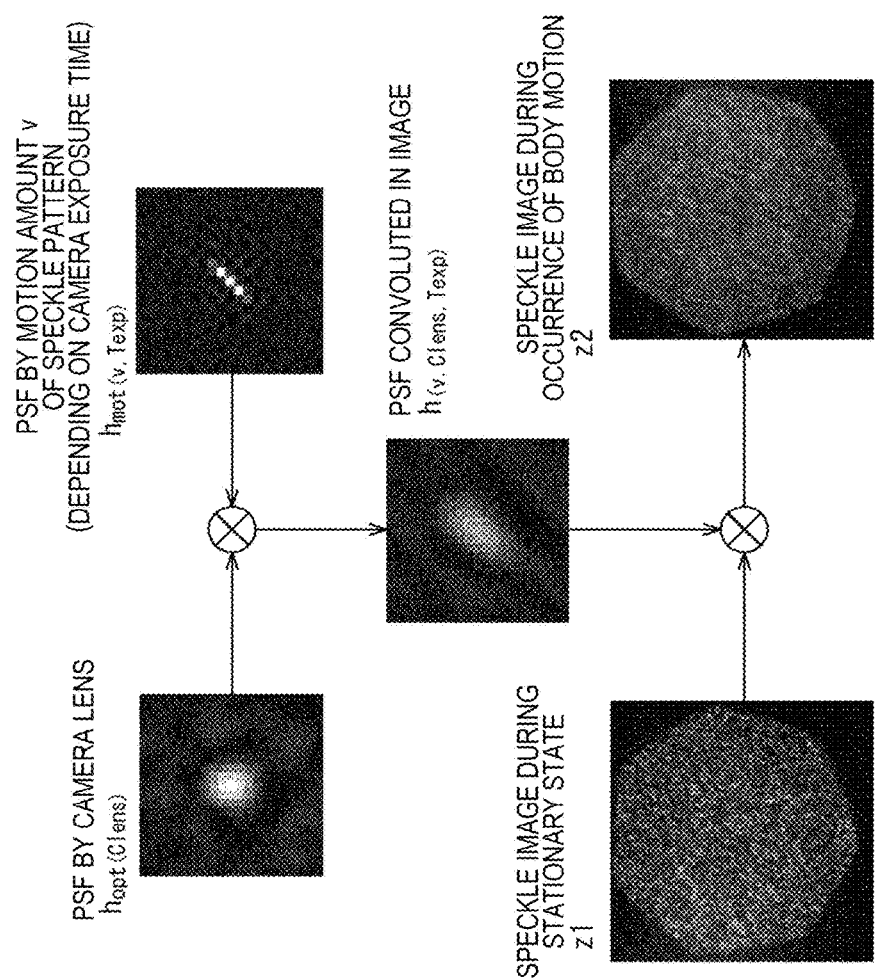
FIG. 10 is a diagram for explaining an occurrence principle of a motion blur.

In steps S201 to S203, similar processes to those in steps S101 to S103 in FIG. 9 are executed.

In step S204, the MTF spatial frequency characteristic is calculated as in the process in step S105 in FIG. 9. The calculation result of the MTF spatial frequency characteristic is supplied from the MTF calculation unit 221 to an estimation unit 222 and the motion blur removing unit 311.

In step S205, the motion blur removing unit 311 removes a motion blur. Specifically, the motion blur removing unit 311 calculate a reciprocal of the value of each spatial frequency of the MTF spatial frequency characteristic ($|H_{(v,Clens,Texp)}(\omega_x,\omega_y)|$ or $|H_{mot(v,Texp)}(\omega_x,\omega_y)|$) Then, the motion blur removing unit 311 performs the convolution integral of the spatial frequency distribution data of the speckle image of the current frame and the reciprocal of the MTF spatial frequency characteristic. That is, the intensity of each spatial frequency of the spatial frequency distribution data of the speckle image of the current frame is multiplied by a gain which is the reciprocal of the value of each spatial frequency of the MTF spatial frequency characteristic. As a result, the motion blur component is removed from the spatial frequency distribution data.

Note that, when the gain of each spatial frequency is too large, it causes the occurrence of an artifact. Accordingly, adjustment may be made as appropriate instead of using an exact reciprocal of the MTF spatial frequency characteristic.

The motion blur removing unit 311 supplies the spatial frequency distribution data from which the motion blur component has been removed to the complex conjugate calculation unit 112, the cross-power spectrum calculation unit 121, and the state determination unit 213.

In step S206, the cross-correlation coefficient map is generated as in the above-described process in step S4 in FIG. 4. However, unlike the process in step S4 in FIG. 4, the cross-correlation coefficient map is generated on the basis of the spatial frequency distribution data from which the motion blur component has been removed. Therefore, it is possible to suppress the occurrence of the pseudo peak in the cross-correlation coefficient map, whereby the estimation accuracy of the pulse motion amount is improved. Furthermore, since the occurrence of the pseudo peak is suppressed, a process load of the estimation unit 222 can be mitigated.

Thereafter, in steps S207 to S210, similar processes to those in steps S106 to S109 in FIG. 9 are executed.

In step S211, the complex conjugate of the spatial frequency distribution data is calculated as in the process in step S8 in FIG. 4. However, unlike the process in step S8 in FIG. 4, the complex conjugate of the spatial frequency distribution data from which the motion blur component has been removed is calculated. Then, the spatial frequency distribution data from which the motion blur component has been removed is used for calculation of the cross-power spectrum in the next frame.

In step S212, as in the process in step S111 in FIG. 9, it is determined whether the measurement site is stationary. In a case where it is determined that the measurement site is stationary, the process proceeds to step S213.

In step S213, the spatial frequency distribution data during a stationary state is updated as in the process in step S112 in FIG. 9. However, unlike the process in step S111 in FIG. 9, the spatial frequency distribution data during a stationary state is updated with the spatial frequency distribution data from which the motion blur component has been removed.

Thereafter, the process returns to step S201 and the processes after step S201 are executed.

On the other hand, in a case where it is determined in step S212 that the measurement site is not stationary, the process returns to step S201 and the processes after step S201 are executed.

As described thus far, the removal of the motion blur component from the spatial frequency distribution data improves the estimation accuracy of the pulse motion amount and the measurement accuracy of the pulse.

<2. Variations>

Hereinafter, variations of the above-described embodiments of the present technology will be described.

In the above description, the example of estimating the pulse motion amount using the cross-correlation analysis has been indicated, but the present technology can also be applied to a case where the pulse motion amount is estimated using, for example, template matching.

Furthermore, the method of the cross-correlation analysis is not limited to the above-described method and another method can be used.

Additionally, for example, in a case where the state determination unit 213 performs a pattern analysis on the cross-correlation coefficient map and the cross-correlation coefficient map is similar to an autocorrelation coefficient map of the speckle image of the latest frame, the state determination unit 213 may determine that the measurement site is stationary.

Furthermore, for example, the body motion amount estimation unit 211 may generate a frequency histogram of tone values of the speckle image to find out a blur change (=contrast change) on the basis of the fluctuation of an average value or a variance value of the histogram, thereby estimating the body motion amount.

Additionally, the cross-correlation analysis may be performed between frames not adjacent to each other but, for example, two or more frames apart from each other such that the pulse motion amount is estimated on the basis of a result of this analysis.

Furthermore, the present technology can also be applied to the case of measuring a pulse at a measurement site other than the arm (for example, a finger or an earlobe).

Additionally, in addition to the pulse measurement process, the present technology can be applied to a process including the estimation of the motion amount of the speckle pattern of the speckle image.

Furthermore, in addition to the speckle image, the present technology can be applied to the case of estimating the motion amount in an image in which fine particles are substantially uniformly reflected.

{Configuration Example of Computer}

A series of the above-described processes can be executed by hardware as well and also can be executed by software. In a case where the series of the processes is executed by software, a program constituting the software is installed in a computer. Herein, the computer includes a computer built into dedicated hardware and a computer capable of executing various functions when installed with various programs, for example, a general-purpose personal computer.

Figure 16:
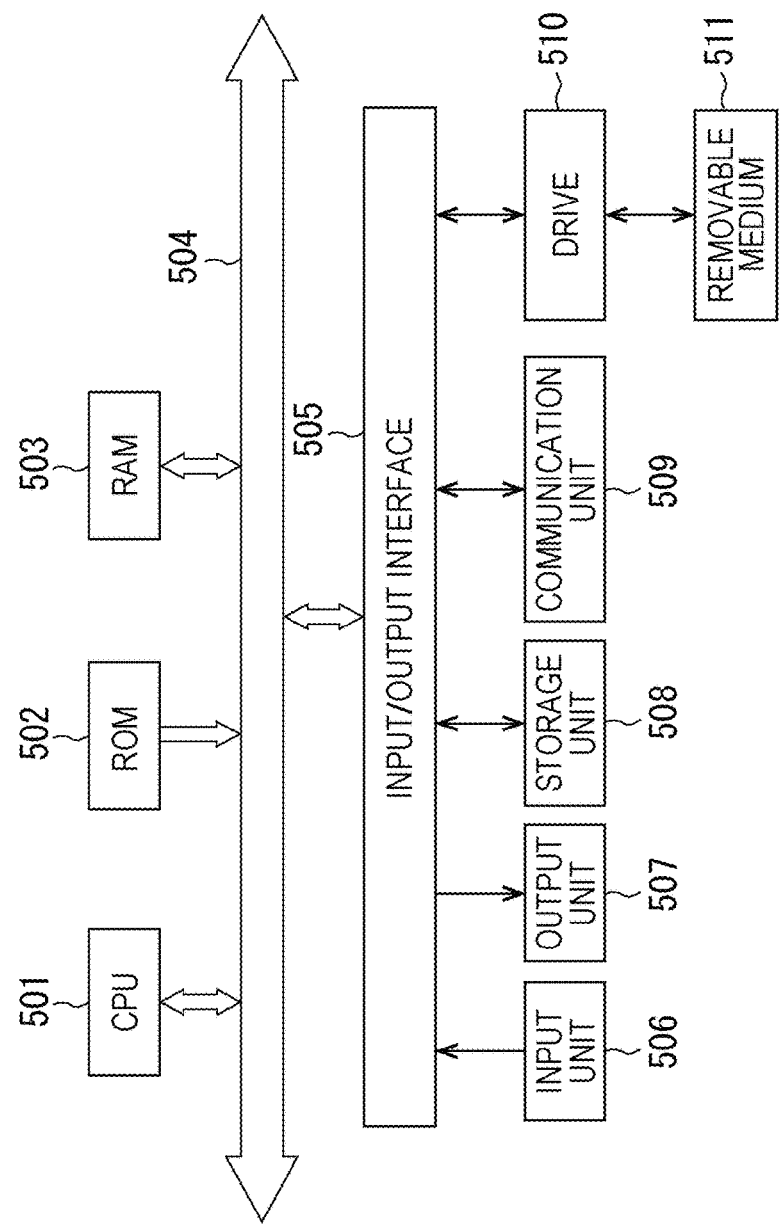
FIG. 16 is a block diagram illustrating a configuration example of a computer.

FIG. 16 is a block diagram illustrating a hardware configuration example of a computer that executes the above-described series of the processes using a program.

In the computer, a central processing unit (CPU) 501, a read only memory (ROM) 502, and a random access memory (RAM) 503 are interconnected through a bus 504.

Additionally, an input/output interface 505 is connected to the bus 504. An input unit 506, an output unit 507, a storage unit 508, a communication unit 509, and a drive 510 are connected to the input/output interface 505.

The input unit 506 includes a keyboard, a mouse, and a microphone. The output unit 507 includes a display and a speaker. The storage unit 508 includes a hard disk and a non-volatile memory. The communication unit 509 includes a network interface. The drive 510 drives a removable medium 511 such as a magnetic disk, an optical disc, a magneto-optical disk, or a semiconductor memory.

In the computer configured as described above, for example, the above-described series of the processes is performed in such a manner that the CPU 501 loads a program stored in the storage unit 508 to the RAM 503 via the input/output interface 505 and the bus 504 to execute.

For example, the program executed by the computer (CPU 501) can be provided by being recorded in the removable medium 511 serving as a package medium or the like. Furthermore, the program can be provided via a wired or wireless transmission medium such as a local area network, the Internet, or digital satellite broadcasting.

In the computer, the program can be installed to the storage unit 508 via the input/output interface 505 by mounting the removable medium 511 in the drive 510. Furthermore, the program can be installed to the storage unit 508 via a wired or wireless transmission medium when received by the communication unit 509. As an alternative manner, the program can be installed to the ROM 502 or the storage unit 508 in advance.

Note that, the program executed by a computer may be a program in which the processes are performed along the time series in accordance with the order described in the present specification, or alternatively, may be a program in which the processes are performed in parallel or at a necessary timing, for example, when called.

Furthermore, in the present specification, a system refers to a collection of a plurality of constituent members (e.g., apparatuses and modules (parts)) and whether all the constituent members are arranged within the same cabinet is not regarded as important. Therefore, a plurality of apparatuses accommodated in separate cabinets so as to be connected to one another via a network and one apparatus of which a plurality of modules is accommodated within one cabinet are both deemed as systems.

In addition, the embodiments according to the present technology are not limited to the above-described embodiments and various modifications can be made without departing from the scope of the present technology.

For example, the present technology can employ a cloud computing configuration in which one function is divided and allocated to a plurality of apparatuses so as to be processed in coordination thereamong via a network.

Furthermore, the respective steps described in the aforementioned flowcharts can be executed by a plurality of apparatuses each taking a share thereof as well as executed by a single apparatus.

Additionally, in a case where a plurality of processes is included in one step, the plurality of processes included in one step can be executed by a plurality of apparatuses each taking a share thereof as well as executed by a single apparatus.

Furthermore, the effects described in the present specification merely serve as examples and not construed to be limited. There may be another effect.

In addition, the embodiments according to the present technology are not limited to the above-described embodiments and various modifications can be made without departing from the scope of the present technology.

Furthermore, note that, for example, the present technology can be also configured as described below.

(1)

An information processing apparatus including:

a cross-correlation analysis unit that performs a cross-correlation analysis between a first image and a second image obtained by capturing the same object as an object of the first image before the first image;

a first motion estimation unit that estimates a first motion amount corresponding to a motion blur in the first image; and a second motion estimation unit that estimates a second motion amount different from the first motion amount between the first image and the second image on the basis of a result of the cross-correlation analysis and an estimation result of the first motion amount.

(2)

The information processing apparatus according to the aforementioned (1), in which the second motion estimation unit estimates the second motion amount by detecting a motion vector on the basis of a result of the cross-correlation analysis and limits a region for detecting the motion vector on the basis of an estimation result of the first motion amount.

(3)

The information processing apparatus according to the aforementioned (1) or (2), further including a spatial frequency analysis unit that analyzes a first spatial frequency distribution of the first image and a second spatial frequency distribution of the second image, in which the cross-correlation analysis unit performs a cross-correlation analysis between the first image and the second image on the basis of the first spatial frequency distribution and the second spatial frequency distribution.

(4)

The information processing apparatus according to the aforementioned (3), in which the first motion estimation unit includes:

a transfer function calculation unit; and an estimation unit, the transfer function calculation unit calculates a first transfer function representing a characteristic of the motion blur in the first image on the basis of the first spatial frequency distribution and a stationary spatial frequency distribution which is a spatial frequency distribution of an image while the object is substantially stationary, and the estimation unit estimates the first motion amount on the basis of the first transfer function.

(5)

The information processing apparatus according to the aforementioned (4), in which the transfer function calculation unit calculates the transfer function on the basis of a ratio of intensity of each spatial frequency between the first spatial frequency distribution and the stationary spatial frequency distribution.

(6)

The information processing apparatus according to the aforementioned (4) or (5), further including a state determination unit that sets the stationary spatial frequency distribution to be used next with the first spatial frequency distribution in a case where it is determined that the object is substantially stationary in the first image.

(7)

The information processing apparatus according to any one of the aforementioned (4) to (6), further including a motion blur removing unit that removes a component of a motion blur from the spatial frequency distribution of an image, in which the transfer function calculation unit calculates a second transfer function representing a characteristic of a motion blur in the second image on the basis of the second spatial frequency distribution and the stationary spatial frequency distribution, the motion blur removing unit removes a component of the motion blur in the first image from the first spatial frequency distribution on the basis of the first transfer function and removes a component of the motion blur in the second image from the second spatial frequency distribution on the basis of the second transfer function, and the cross-correlation analysis unit performs a cross-correlation analysis between the first image and the second image on the basis of the first spatial frequency distribution and the second spatial frequency distribution from which the components of the motion blurs have been removed.

(8)

The information processing apparatus according to any one of the aforementioned (1) to (7), in which the object is a measurement site for measuring a pulse of a subject, and the information processing apparatus further including a pulse measurement unit that measures a pulse of the subject on the basis of an estimation result of the second motion amount.

(9)

The information processing apparatus according to the aforementioned (8), in which the first motion amount is a motion amount due to a body motion of the subject, and the second motion amount is a motion amount due to a pulse of the subject.

(10)

An information processing method including:

a cross-correlation analysis step of performing a cross-correlation analysis between a first image and a second image obtained by capturing the same object as an object of the first image before the first image;

a first motion estimation step of estimating a first motion amount corresponding to a motion blur in the first image; and a second motion estimation step of estimating a second motion amount different from the first motion amount between the first image and the second image on the basis of a result of the cross-correlation analysis and an estimation result of the first motion amount.

(11)

A program for causing a computer to execute processes including:

a cross-correlation analysis step of performing a cross-correlation analysis between a first image and a second image obtained by capturing the same object as an object of the first image before the first image;

a first motion estimation step of estimating a first motion amount corresponding to a motion blur in the first image; and a second motion estimation step of estimating a second motion amount different from the first motion amount between the first image and the second image on the basis of a result of the cross-correlation analysis and an estimation result of the first motion amount.

REFERENCE SIGNS LIST

1 Measurement apparatus
11 Main body unit
22 Light-emitting element
23 Camera
26, 26a to 26c Information processing unit
101 Motion detection unit
102 Pulse measurement unit
111 Spatial frequency analysis unit
112 Complex conjugate calculation unit
114 Cross-correlation analysis unit
115 Pulse motion amount estimation unit
121 Cross-power spectrum calculation unit
122 Cross-correlation map generation unit
201 Motion detection unit
211 Body motion amount estimation unit
212 Pulse motion amount estimation unit
213 State determination unit
221 MTF calculation unit
222 Estimation unit
301 Motion detection unit
311 Motion blur removing unit

The invention claimed is:

1. An information processing apparatus comprising:
a processing device and a memory containing instructions that, when executed by the processing device, are configured to:
perform a cross-correlation analysis between a first image and a second image obtained by capturing the same object as an object of the first image before the first image;
estimate a first motion amount corresponding to a motion blur in the first image; and
estimate a second motion amount different from the first motion amount between the first image and the second image on the basis of a result of the cross-correlation analysis and an estimation result of the first motion amount.

2. The information processing apparatus according to claim 1, wherein the instructions are further configured to:
estimate the second motion amount by detecting a motion vector on the basis of a result of the cross-correlation analysis and limit a region for detecting the motion vector on the basis of an estimation result of the first motion amount.

3. The information processing apparatus according to claim 1, wherein the instructions are further configured to:
analyze a first spatial frequency distribution of the first image and a second spatial frequency distribution of the second image, wherein
a cross-correlation analysis between the first image and the second image is performed on the basis of the first spatial frequency distribution and the second spatial frequency distribution.

4. The information processing apparatus according to claim 3, wherein the instructions are further configured to:

calculate a first transfer function representing a characteristic of the motion blur in the first image on the basis of the first spatial frequency distribution and a stationary spatial frequency distribution which is a spatial frequency distribution of an image while the object is substantially stationary, and estimate the first motion amount on the basis of the first transfer function.

5. The information processing apparatus according to claim 4, wherein the instructions are further configured to:

calculate the transfer function on the basis of a ratio of intensity of each spatial frequency between the first spatial frequency distribution and the stationary spatial frequency distribution.

6. The information processing apparatus according to claim 4, wherein the instructions are further configured to:

set the stationary spatial frequency distribution to be used next with the first spatial frequency distribution in a case where it is determined that the object is substantially stationary in the first image.

7. The information processing apparatus according to claim 4, wherein the instructions are further configured to:

remove a component of a motion blur from the spatial frequency distribution of an image, calculate a second transfer function representing a characteristic of a motion blur in the second image on the basis of the second spatial frequency distribution and the stationary spatial frequency distribution, remove a component of the motion blur in the first image from the first spatial frequency distribution on the basis of the first transfer function and remove a component of the motion blur in the second image from the second spatial frequency distribution on the basis of the second transfer function, and perform a cross-correlation analysis between the first image and the second image on the basis of the first spatial frequency distribution and the second spatial frequency distribution from which the components of the motion blurs have been removed.

8. The information processing apparatus according to claim 1, wherein the object is a measurement site for measuring a pulse of a subject, and the instructions are further configured to measure a pulse of the subject on the basis of an estimation result of the second motion amount.

9. The information processing apparatus according to claim 8, wherein the first motion amount is a motion amount due to a body motion of the subject, and the second motion amount is a motion amount due to a pulse of the subject.

10. An information processing method comprising:

a cross-correlation analysis step of performing a cross-correlation analysis between a first image and a second image obtained by capturing the same object as an object of the first image before the first image;

a first motion estimation step of estimating a first motion amount corresponding to a motion blur in the first image; and a second motion estimation step of estimating a second motion amount different from the first motion amount between the first image and the second image on the basis of a result of the cross-correlation analysis and an estimation result of the first motion amount.

11. A non-transitory computer-readable medium containing instructions that, when executed by a processing device, perform an information processing method comprising:

a cross-correlation analysis step of performing a cross-correlation analysis between a first image and a second image obtained by capturing the same object as an object of the first image before the first image;

a first motion estimation step of estimating a first motion amount corresponding to a motion blur in the first image; and a second motion estimation step of estimating a second motion amount different from the first motion amount between the first image and the second image on the basis of a result of the cross-correlation analysis and an estimation result of the first motion amount.

* * * * *